United States Patent [19]
Fuisz et al.

[11] Patent Number: 6,083,430
[45] Date of Patent: *Jul. 4, 2000

[54] METHOD OF PREPARING A DOSAGE UNIT BY DIRECT TABLETING AND PRODUCT THEREFROM

[75] Inventors: Richard C. Fuisz, McLean, Va.; Garry L. Myers, Kingsport, Tenn.; Robert K. Yang, Flushing, N.Y.; Mark R. Herman, Nokesville, Va.; Whitney S. Cavanagh, Reston, Va.; John R. Sisak, Fairfax, Va.; Andrea S. Brothers, Chantilly, Va.

[73] Assignee: Fuisz Technologies Ltd., Chantilly, Va.

[ * ] Notice: This patent is subject to a terminal disclaimer.

[21] Appl. No.: 08/642,026

[22] Filed: Apr. 29, 1996

Related U.S. Application Data

[63] Continuation-in-part of application No. 08/330,412, Oct. 28, 1994, Pat. No. 5,683,720.

[51] Int. Cl.⁷ ......................................................... A61K 9/14
[52] U.S. Cl. ...................... 264/5; 264/7; 264/8; 424/489; 424/490; 424/493
[58] Field of Search ..................................... 424/489, 490, 424/493; 426/515, 512; 264/5, 7, 8; 241/15

[56] References Cited

U.S. PATENT DOCUMENTS

| | | |
|---|---|---|
| 1,586,716 | 6/1926 | Snow, Jr. . |
| 1,678,562 | 7/1928 | Edens . |
| 2,470,298 | 4/1949 | Fields . |
| 2,478,715 | 8/1949 | Schmidt . |
| 3,155,573 | 11/1964 | Fowler . |
| 3,605,738 | 9/1971 | Ciranna . |
| 4,079,125 | 3/1978 | Sipos . |
| 4,132,753 | 1/1979 | Blichare et al. . |
| 4,184,258 | 1/1980 | Barrington et al. . |
| 4,323,523 | 4/1982 | Ueda et al. . |
| 4,534,345 | 8/1985 | Wetterlin . |
| 4,855,326 | 8/1989 | Fuisz . |
| 4,876,094 | 10/1989 | Benton et al. . |
| 4,948,622 | 8/1990 | Kokubo et al. . |
| 4,971,805 | 11/1990 | Kitanishi et al. . |
| 4,997,856 | 3/1991 | Fuisz . |
| 5,055,306 | 10/1991 | Bary et al. . |
| 5,078,129 | 1/1992 | Kleinberg et al. . |
| 5,183,493 | 2/1993 | Brandau et al. . |
| 5,204,108 | 4/1993 | Illum . |
| 5,213,810 | 5/1993 | Steber . |
| 5,318,523 | 6/1994 | Lu . |
| 5,456,677 | 10/1995 | Spector . |
| 5,458,823 | 10/1995 | Perkins et al. ............................... 264/8 |
| 5,464,632 | 11/1995 | Cousin et al. ........................... 424/465 |
| 5,470,311 | 11/1995 | Setterstrom et al. . |
| 5,683,720 | 11/1997 | Myers et al. ............................. 424/489 |
| 5,728,397 | 3/1998 | Fuisz ....................................... 424/401 |

OTHER PUBLICATIONS

FMC Corporation, Pharmaceutical Division, Product Information Sheets on AviSphere^SM System, AviSpheres™, Drug Loaded Spheres, Copyright 1993 FMC Corporation.

*Primary Examiner*—Jeffrey Mullis
*Attorney, Agent, or Firm*—John F. Levis; Hoffman & Baron

[57] ABSTRACT

The present invention is a process and apparatus for making a dosage unit by direct tableting of shearlite particles. The present invention also includes the dosage unit itself. Shearlite particles, which are prepared by subjecting a feedstock material to liquiflash processing, can be directly fed from a shearlite device to a tableting apparatus without the necessity of any intermediate steps or additional ingredients to facilitate flowability or tablet formation.

12 Claims, 27 Drawing Sheets

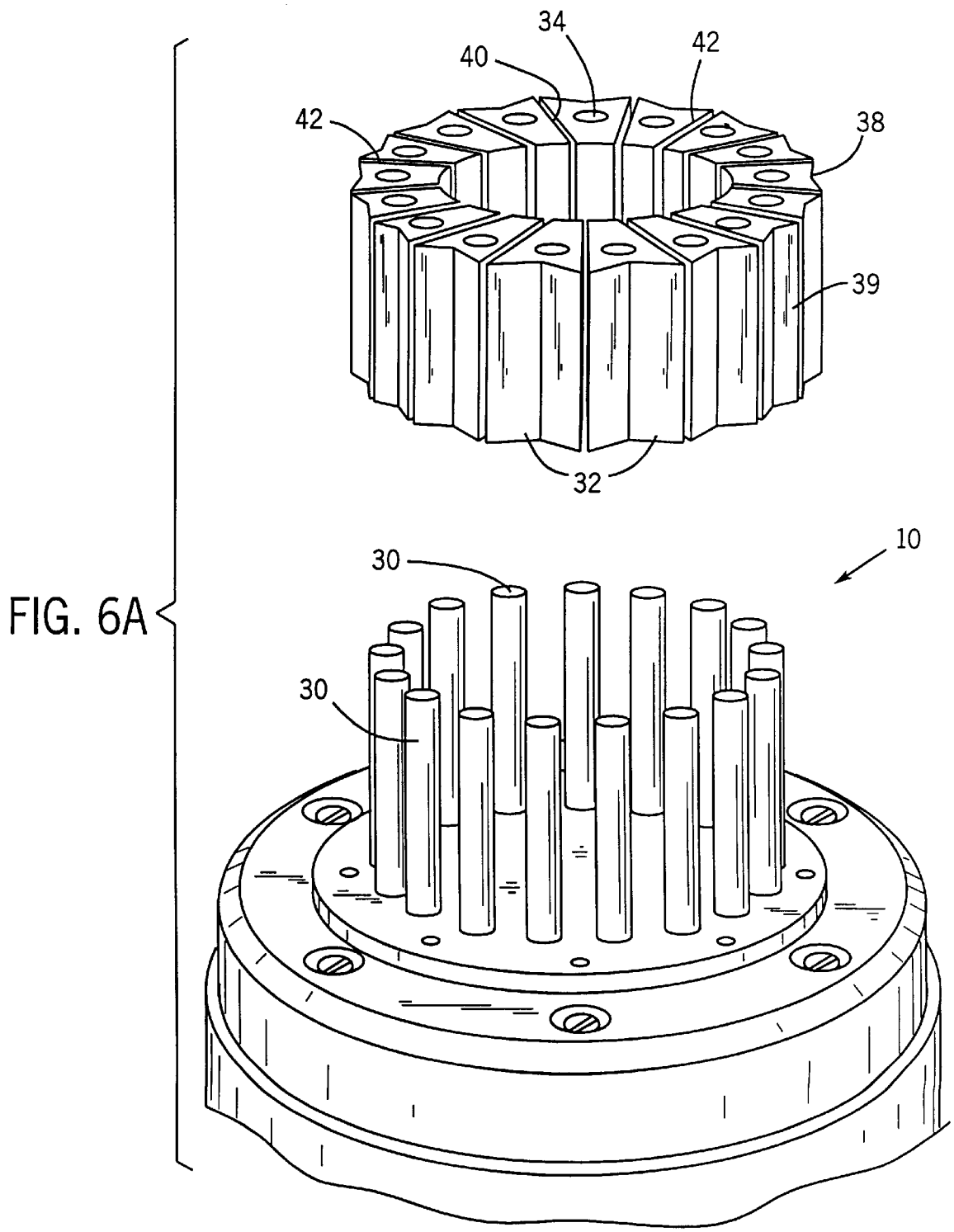

FIG. 8
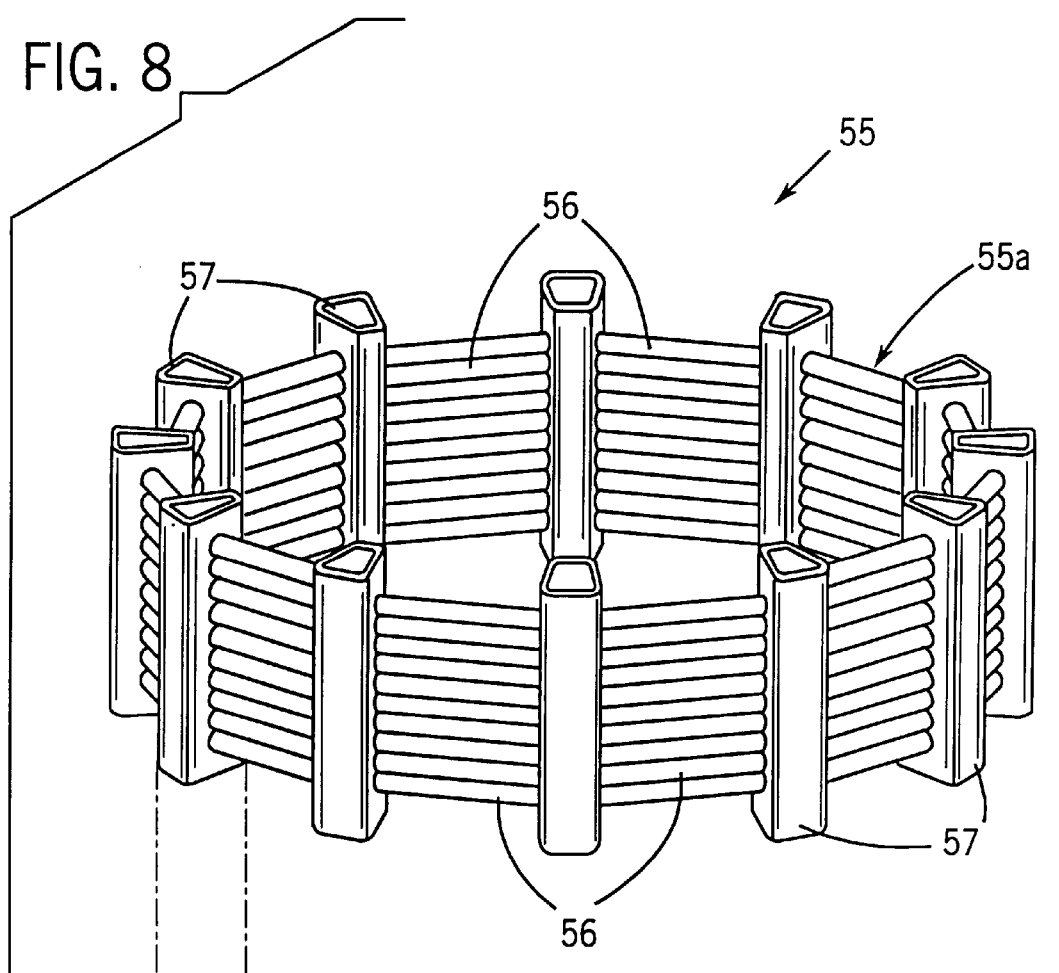
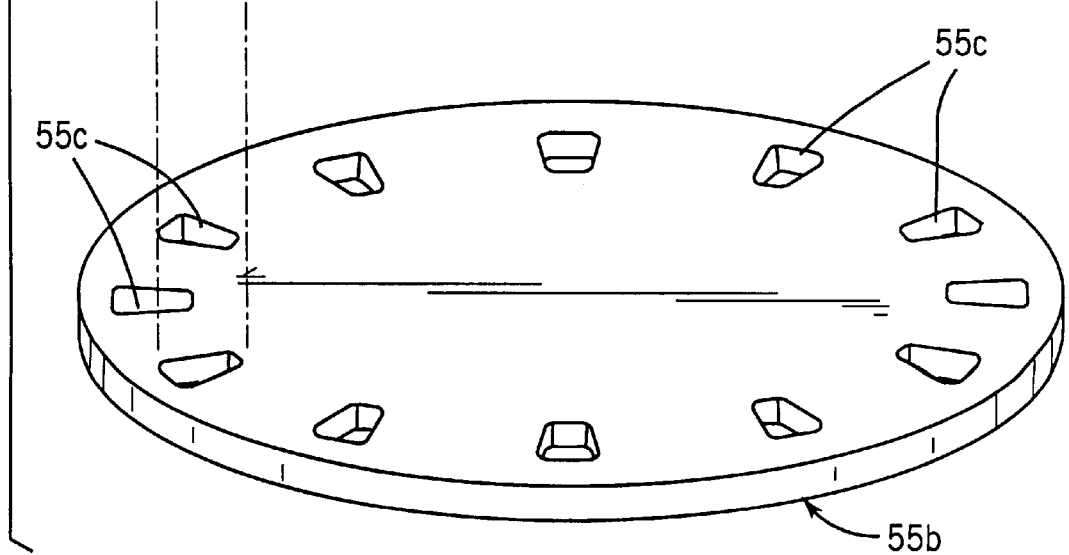

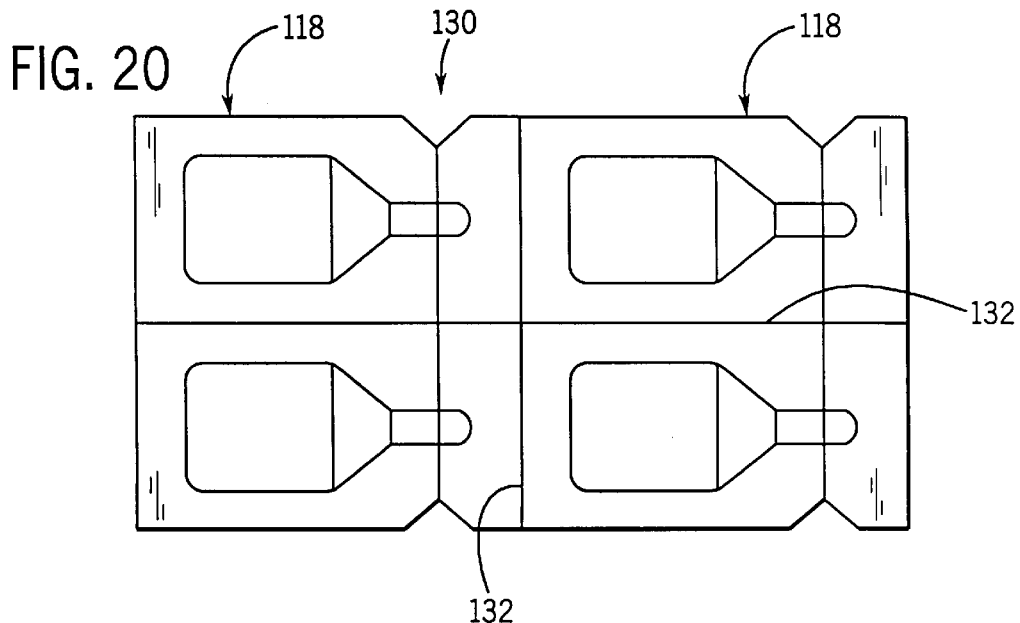
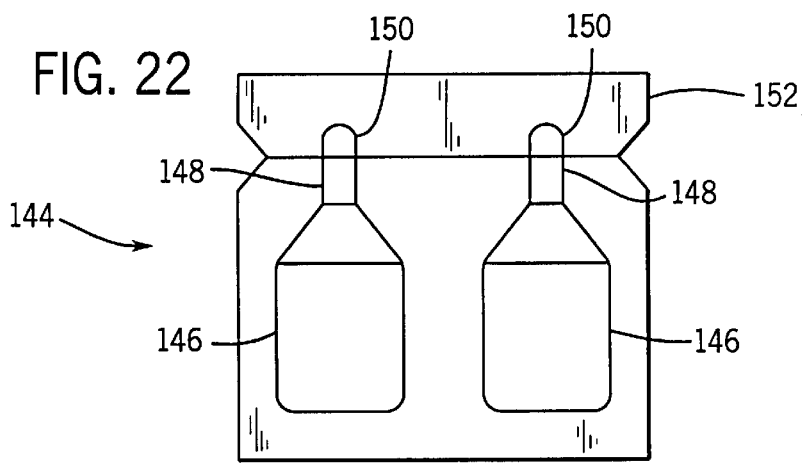
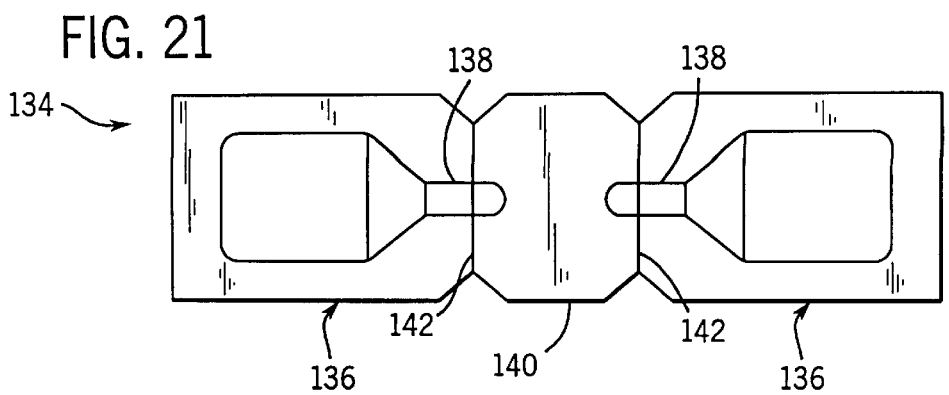

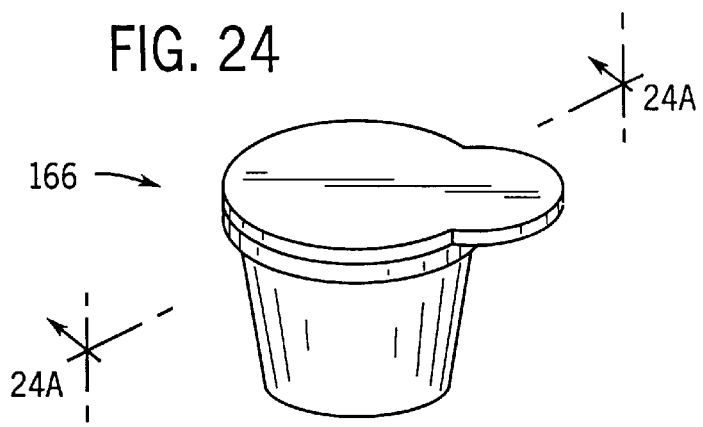
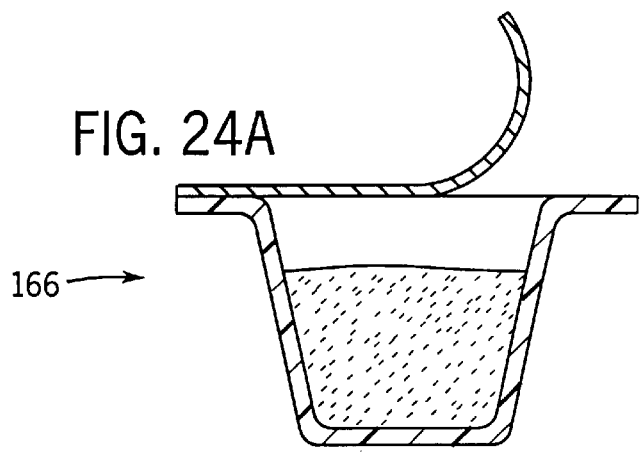
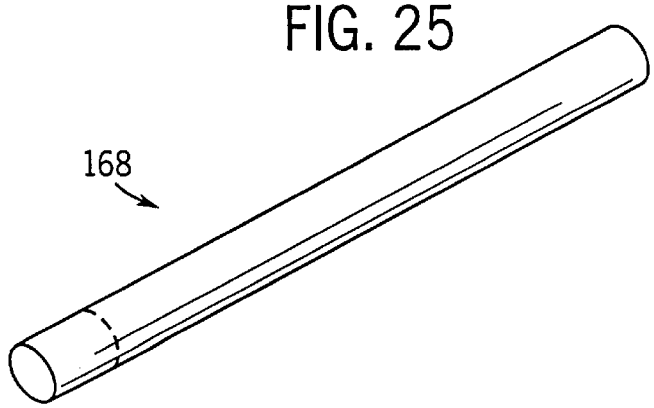
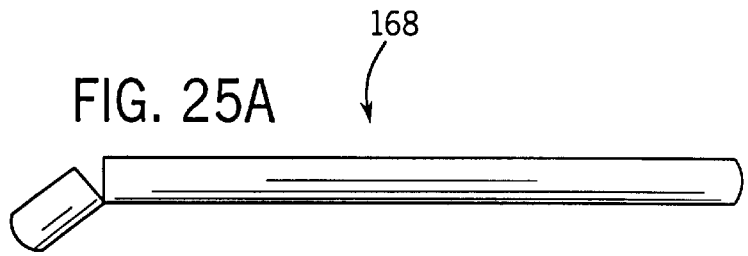

METHOD OF PREPARING A DOSAGE UNIT BY DIRECT TABLETING AND PRODUCT THEREFROM

This application is a continuation-in-part application of U.S. application Ser. No. 08/330,412 filed Oct. 28, 1994 now U.S. Pat. No. 5,683,720.

BACKGROUND OF THE INVENTION

The present invention relates to the preparation of dosage units for delivering bio-affecting agents, e.g., compressed tablets, and, in particular, relates to improved methods of manufacturing such units, as well as improved ingredients therefor.

Compressed tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

The preparation of formulations for tableting by wet granulation is the oldest method and still the most widely used. Wet granulation involves many steps, including: milling of drugs and excipients, mixing of the milled powders, preparation of binder solution, mixing of the milled powders, preparation of binder solution, mixing of binder solution with powder mixture to form a wet mass, coarse screening of the wet mass using 6–12 mesh screens, drying of moist granules, screening of dry granules with lubricant and disintegrant, and tablet compression.

Wet granulation is an expensive process because it requires many processing steps and involves considerable material handling equipment. Consequently, the process requires both energy and substantial space which should be environmentally controlled.

Dry granulation refers to the granulation of a powder mixture by compression without the use of heat and solvent. Dry granulation is used when wet granulation is not available because the drug is sensitive to moisture or heat.

Two methods are used for dry granulation. One method is slugging, where the powder is precompressed on a heavy-duty tablet press, and the resulting tablets or slugs are milled to yield the granulation. The other method is precompression of the powder with pressure rolls using a compactor.

Dry granulation has many disadvantages. It requires a specialized heavy-duty tablet press to form the slug; it does not permit uniform color distribution as can be achieved with wet granulation, where dye can be incorporated into the binder liquid; the pressure roll press cannot be used with insoluble drugs because this may retard the dissolution rate; and the process tends to create dust thereby increasing the potential for cross-contamination.

Direct compression tableting has the least amount of steps. Direct compression is used in a process by which tablets are compressed directly from powder blends of the active ingredient and suitable excipients (including fillers, disintegrants, and lubricants) which are included in the mix to provide uniform flow into the die cavity and form a firm solid compression tablet. No pretreatment of the powder blends by wet or dry granulation procedures is necessary.

Although it has considerably fewer steps than either wet or dry granulation processes, direct compression also has many technological limitations. These limitations include primarily obtaining sufficient flow, and obtaining bonding of particles to form a strong compressed tablet. Low-dose drugs are difficult to blend, that is, uniform distribution of the drug is not easily attained and unblending sometimes occurs during the compression stage. High-dose drugs do not lend themselves to direct compression because of poor flowability and poor compressibility. A typical example would be some of the antacid drugs, such as aluminum hydroxide and magnesium carbonate.

When direct compression is used the choice of excipients is extremely critical. It is desirable that when using direct compression fillers and binders possess both compressibility and fluidity. In addition to compressibility failures, the process of direct compression also has disadvantages in the area of blending. Direct compression blends are subject to unblending in post blending handling steps. Differences in particle size because of differences in density between drug and excipient particles may also lead to unblending in the hopper or feedframe on the tablet press.

A disadvantage of all prior art process is the production of fines usually associated with making compression tablets. In the prior art, preparation of particles for formulation of tablets by compression results in a noticeable amount of fines, i.e., very tiny particles on the order of 150 microns and less. Fines interfere with operation of apparatus for feeding tableting machines as well as the operation of the tableting machines. Often, it is necessary to conduct tablet production in a facility which is environmentally controlled to eliminate or reduce the fines. This adds to the cost of production of the tablets.

Moreover, a percentage of the non-compressed particulate is lost during production because there are fines dispersed and cannot be recaptured, and because some of the fines are not capable of being recovered for recycle.

It is desirable to provide a method for direct compression tablet manufacturing which includes advantages of wet and dry granulation and traditional direct compression but does not have the disadvantages associated therewith.

In commonly owned U.S. Pat. No. 4,855,326 to Fuisz, the inventor has previously disclosed that a fiber form of medicament-bearing product can be compacted to form a sheet-like body. He cautions, however, that the compact body cannot be squeezed too much for fear of breaking the fibrous mass. There is no indication to form a compressed tablet as a medicinal dosage form.

Similarly, in U.S. Pat. No. 4,873,085 a spun fibrous cosmetic is disclosed as well as a compacted form of sugar fibers to form a sheet-like body which can be handled more readily. There is no indication to form a compressed tablet.

In U.S. Pat. No. 4,997,856, a wafer-like structure is disclosed in which a medicament is distributed on or through spun fibers which are then chopped by passing through a conventional "food grinder" (Hobart hamburger grinder). The enclosed volume of the end product is less than 30%, and preferably less than 15%, of the as-spun volume of floss. There is no mention in the '856 disclosure to form a compressed tablet.

The use of compacted spun fibers in the same sense as in the patents mentioned above is also disclosed in U.S. Pat. No. 5,034,421 and U.S. Pat. No. 5,096,492. None of these disclosures suggest formation of a compressed tablet.

Commonly-owned, copending U.S. application Ser. No. 08/194,682 filed Feb. 10, 1994 discloses a method for making edible units and product therefrom made by compressing shearform matrix masses sufficiently to form a comestible compression unit. Commonly-owned copending U.S. application Ser. No. 08/259,258 filed Jun. 14, 1994 discloses a method for preparing a quick-dissolve comestible unit by initiating crystallization of shearform matrix and combining with an additive, either before or after initiating crystallization, to form flowable, compactible micro-particulates and then subjecting the result micro-particulates to compacting, and the product therefrom. Commonly-owned copending U.S. application Ser. No. 08/259,496 filed Jun. 14, 1994 discloses a method of preparing a rapidly dissolving comestible unit by mixing uncured shearform matrix and an additive, molding a unit dosage form, and curing the matrix in the molded condition, and the product therefrom.

The above-identified parent application, which is incorporated herein by reference, describes a method for preparing discrete particles and the product resulting from the inventive method. Particles resulting from this method have highly consistent size and shape, which is substantially spheroidal. Thus, the disclosed method is highly efficient and predictable.

As a result of the consistent size and substantially spheroidal shape, the product has been found to have excellent flow properties. The flow property of a substance as used herein means the ability of the substance to flow. A mass of material can be made to flow by tilting the surface on which a quantity of the material results until it moves under the force of gravity in a direction away from the "at rest" position. A substance with good flow properties will move easily and evenly away from the "at rest" position. Such a material is easily utilized in processing apparatus for preparing compressed tablets, capsules, etc. Substances without good flow properties, do not readily flow, and generally do not move in an even condition. Such substances generally are transported in the form of clumps or uneven masses from the "at rest" position.

It is believed the unique properties of the product set forth in the parent application can be used to improve dosage units prepared by traditional tableting methods.

The present invention is, therefore, intended to overcome the shortcomings found in traditional tablet-making procedures, and to provide a significantly improved method of making tablets. These and other objects of the present invention will be realized by those skilled in the art in view of the following disclosure.

SUMMARY OF THE INVENTION

The present invention is a process for making a dosage unit for delivering a bio-affecting agent and a product resulting from the process. The process includes directly tableting shearlite particles. Shearlite particles are defined herein as discrete particles which are prepared by subjecting a solid organic-based feedstock to liquiflash and shearing conditions. The shearlite particles can be made from an active ingredient, a combination of active ingredients, a non-active ingredient, or a combination of active and non-active ingredients. In fact, it has been found that shearlite particles of non-active ingredients can be beneficially used as excipients in the process of making some of the dosage units of the present invention. "Directly tableting" as used herein means to compress shearlite particles, subsequent to their formation, without any intermediate processing steps or additional ingredients, if so desired. Thus, "directly" is a term identifying the elimination of steps and/or ingredients normally considered essential in traditional tablet making procedures. With reference to wet granulation and dry granulation procedures, the present invention has eliminated many interim steps and ingredients used to obtain the proper size of particles and adequate flowability to enable transport to and through tableting apparatus. The present invention has also removed the requirement for many excipients (e.g., fillers, disintegrants and lubricants), previously considered necessary even in traditional direct compression methods. However, as previously described, excipients in the form of shearlite particles can be beneficially utilized in accordance with the present invention.

Preferably the feedstock used to prepare shearlite particles is a solid organic-based feedstock, capable of being transformed to a liquiform in the substantial absence of a dissolving medium. The feedstock, thus reduced to unimpeded internal flow under liquiflash conditions, is subsequently discretized by natural mass separation of the flowing feedstock in the presence of shear force to form shearlite particles.

"Liquiflash conditions" as used herein means those conditions which provide transformation of a solid to a liquid state and then to the solid state (e.g., solid-liquid-solid) instantaneously. By instantaneously is meant less than seconds, in most cases on the order of fractions of a second, most preferably milli-seconds. Thus, certainly the transformation from solid to liquid to solid takes place in a time period of less than five seconds, preferably less than one second, and most preferably less than 0.1 seconds.

During this rapid transition, shear forces can act on the material to discretize the feedstock. Thus, liquiflash conditions are the combination of temperature and force which induce an organic-based feedstock to flow and re-solidify into a changed shape as it is being discretized by the action of shear force. In preferred embodiments the size and the new shape are highly consistent among the discretized particles. Thus, the shape is preferably spheroidal and the size distribution is very limited with only minor variations.

The highly consistent spheroidal shape and the narrow range of size distribution causes the shearlite particles to flow evenly and easily. The discrete shearlite particles produced are preferably microspheres, which as used herein preferably means not greater than about 500 $\mu$m, more preferably not greater than about 400 $\mu$m, and most preferably not greater than about 300 $\mu$m. In the preferred method of the present invention the liquiflash conditions are provided by a spinning head having a heated peripheral barrier with exit openings provided therethrough for passage of feedstock flowing under centrifugal force. The shear force referred to above is imparted to flowing feedstock by resistance of air pressure against the liquiform feedstock as it exits the spinning head.

The ambient atmosphere can be undisturbed except by the motion of the spinning head. Alternatively, the ambient atmosphere about the spinning head can be a positive counter or concurrent flow adjacent the outside surface of the processing barrier. This permits greater control of separation of the liquiform feedstock.

The discrete particles separated from the mass of flowing feedstock are cooled. In a preferred form of the present invention the discrete particles are monodispersed. "Monodispersed" as used herein refers to the production of a plurality of uniform spherical particulates, e.g., shearlites. As explained hereinabove methods for barrier processing of feedstock known in the art generally results in a product having a wide variety of sizes and shapes. This is due to many factors all of which contribute to a basic lack of control over the formation of particulates.

In the present invention, however, natural mass forming forces available in minute material masses, e.g., entropy, et al., provide a predictable uniform size. Thus, monodispersed means that at least about 40% by weight, preferably at least about 60% by weight and most preferably at least about 80% of the product herein have a largest diameter which is within 60% of the mean particle diameter. Particle diameter is the dimension which is the greatest straight line dimension in the largest plane taken through a three dimensional particulate. Generally, when the particulate is spheroidal in shape, the particulate diameter is the diameter of the spheroid. In a preferred embodiment, monodispersability means that at least 40% of the particulates are within 50% of the mean particulate diameter, and, in a most preferred embodiment, within 40% of the mean particulate diameter.

Processable feedstock materials used in the present invention are predominantly "organic material." Organic material as used herein means carbon containing compounds, e.g., composition and structure of carbon containing compounds, whereas inorganic materials (or compounds) pertain to substances which do not contain organic type carbon. Polycarbon carbon compounds are preferably used in the present invention. Hydrocarbons are a major portion of organic materials, and are also preferred for use herein. Metals, inorganic carbonates and silicates, e.g., glass, are not considered organic materials for purposes of the present invention. Furthermore, proteinaceous material having high molecular weight is not considered "organic material" as used herein.

In a preferred embodiment of the present invention, the feedstock material includes a medicament so that the resulting product can be a delivery system for inclusion in a dosage unit.

Another preferred embodiment is a sucrose product having a highly consistent small size and spheroidal shape. The size range is from 5 $\mu$m to 100 $\mu$m, and is preferably from 10 $\mu$m to 50 $\mu$m—ideally 15 $\mu$–30 $\mu$, centered around 25 $\mu$m.

In one preferred embodiment the shearlite discrete particles consist of a medicament which has a solid spherical body having substantially no discontinuity therein. Consequently, the spherical body can be a substantially pure drug or active ingredient which is at least 80% of the theoretical density of the drug at standard temperature and pressure, and is preferably at least 90%, and most preferably not less than 95% theoretical density.

Preferably, the spherical body or bodies are shearlite microspheres as defined herein. As a result of the present invention drugs or combinations of drugs can be combined with excipients and prepared on a commercial scale to provide spherical particles having a high degree of size consistency. This capability provides a major advantage in the art of preparing controlled released delivery systems.

The product of the present invention can be a true amalgam of different drugs or active components or combinations of amalgams and mixtures of drug and non-drug ingredients, including ingredients previously believed incompatible, interactive or unstable, e.g., vitamin $B_{12}$ and minerals. If two or more drug components included in the feedstock have similar melting points, the product will usually be a true amalgam of the drug components. If one or more of the active ingredients has a higher melting point than one or more of the other components, the higher melting drug will disperse substantially and consistently throughout the liquiform when the lower melting point ingredients are processed. Finally, one of the components, such as the low melting point ingredient, can be a non-active ingredient. For example, sucrose can be used in combination with active ingredients to form a spherical particulate product having an active ingredient substantially and evenly distributed throughout. One particularly useful combination of active agents includes agents used as cough and cold treatment.

In preferred embodiments of this aspect of the invention, the feedstock can be a saccharide based material, preferably, a sugar. Alternatively, the feedstock material can itself be a medicament which includes one or more active agents.

The medicaments contemplated for use in this aspect of the invention include one or more active agents as set forth hereinbelow. Controlled-release substances are those which are known in the art, some of which have been set forth with specificity in the present disclosure. Taste-altering substances include taste-masking substances, sweeteners, flavorings, and, in general, any substance which changes the natural organoleptic perception of the product resulting from the liquiflash processing.

In a further preferred embodiment of the present invention, the medicament includes an anti-inflammatory substance which is a non-steroidal anti-inflammatory agent selected from the group consisting of salicylates, acetic acids, propionic acids, fenamates, oxicams, and tenidap. A particularly preferred non-steroidal anti-inflammatory agent is ibuprofen which is a propionic acid anti-inflammatory agent. Other propionic acid anti-inflammatory agents includes flurbiprofen, naproxen, and ketoprofen.

In yet another preferred embodiment of the present invention, the medicament includes $H_2$-antagonists as an active agent.

In another embodiment of the present invention, the dosage units can include, in addition to the shearlite particles of medicament described above, shearlite particles of non-active ingredients as excipients. Preferably, the excipient shearlite particles are formed from a feedstock of a saccharide based material that has been subjected to liquiflash conditions. Examples of saccharide based materials include sugars such as sucrose, sugar alcohols such as mannitol, and mixtures thereof.

Alternatively, dosage units of the present invention can be formed from the shearlite particles of medicament mentioned above and an excipient material in a non-shearlite condition, e.g., a floss or powder.

Another aspect of the present invention is an apparatus for making dosage unit which includes a shearlite particle making device ("shearlite device") connected for direct feed of shearlite particles to a tablet-making machine. The shearlite device is one such as that described in the parent application, and tablet-making machine similar to those known in the art can be used in the present invention. Direct feed from the shearlite device to the tablet-making machine can be a particulate conveyor (e.g., conduit, tray, track, etc.) which is used to transfer shearlite particles and is used herein to identify the lack of required assisting mechanisms.

As a result of the present invention, substances which are known to require multiple preparation steps and/or additional ingredients to prepare a tablet, can now be tableted without such steps and/or ingredients.

For example, ascorbic acid, which was previously considered tabletable only after preparation with additional steps and ingredients, can now be directly tableted in the sense of the present invention.

Another advantage of the present invention is that excipients can be provided having a particle size and shape thoroughly compatible with the active-containing shearlite particles. This condition, in turn, provides complete physical homogeneity and enhances machine handling of the tableting formulation. More specifically, it has been found that the excellent flowability of the tableting formulation to the tableting apparatus is maintained while utilizing non-active shearlite particles as an excipient.

Other and further advantages of the present invention will be realized by those skilled in the art in view of the disclosure set forth herein, and it is intended to include all such advantages as part of the present invention, and to be included within the scope of the claims appended hereto.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIGS. 6A and 6B depict another shearlite device used in the process of the present invention;

FIG. 8 depicts yet another shearlite device used in the present invention;

FIG. 20 depicts a view of a multiple-vessel arrangement of the recipient-dosage delivery system of FIG. 19;

FIG. 21 depicts an alternative multi-vessel arrangement of recipient-dosage delivery systems;

FIG. 22 depicts a multiple dosage recipient-dosage delivery system;

FIG. 24 depicts a cup-shaped vessel for use with the present delivery system;

FIG. 24A is a sectional view of the vessel of FIG. 24;

FIG. 25 depicts an elongate tubular-shaped vessel for use with the present delivery system;

FIG. 25A depicts the vessel of FIG. 25 with the breakaway lid in the open position;

DETAILED DESCRIPTION OF THE INVENTION

Figure 1A:
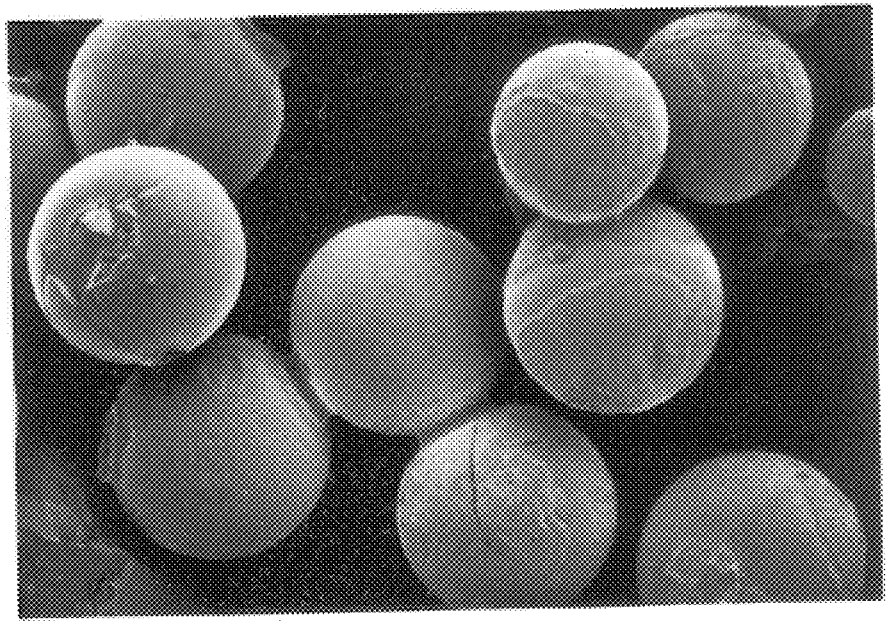
FIGS. 1A and 1B, are photomicrographs at 125× magnification of acetaminophen before and after processing in accordance with the present invention.

The present invention includes a method of making a compression tablet. The tablet possesses a rigid structure and a surface which has hardness, i.e., resists penetration and deformation. In the prior art, compression tablets are produced by a complex arrangement of machinery required to implement several processing steps and/or to incorporate several ingredients necessary to feed a tablet mold and form a tablet.

The present invention improves the art of tableting because it reduces the requirement for several processing steps and additional ingredients which facilitate flow through the apparatus. Moreover, the process is improved so that other drawbacks associated with the prior art, such as production of fines, are reduced or eliminated.

Tableting machines useful for preparing compression tablets usually include a die and a punch. Feeding mechanisms direct the granulation to the die cavity and punches compress the tablet once the granulation has been placed in the die cavity. The tablet press may be a single station (or single punch press) or, alternatively, a multistation (e.g., rotary) press.

In commonly-owned, copending U.S. application Ser. No. 08/194,682, filed Feb. 10, 1994, a material is fed to a tableting machine as a free-form agglomerate in which selected ingredients, such as a medicinal substance, and a carrier material are fused together. The free-form agglomerate is distinguished from agglomerates formed from wet and dry granulations, but they are not shearlite particles.

The method of the present invention, however, is implemented by use of shearlite particles. Shearlite particles are prepared by subjecting a feedstock capable of being transformed to liquiform in the absence of a dissolving medium to liquiflash conditions to provide substantially unimpeded internal flow. The feedstock contemplated for use in the present invention is a feedstock which is capable of being transformed instantaneously from a solid to a liquid and back to a solid.

It has become known to those skilled in the art of material processing, and, especially to artisans familiar with the technology of the owner of the present invention, that "flash flow" refers to conditions of temperature and force required to transform a solid feedstock to a new solid having a different morphology and/or chemical structure in the absence of a heat history. Flash flow can be implemented by "flash heat" processing. The term flash heat is understood to mean a process which includes subjecting the feedstock to combinations of temperature, thermal gradients, flow, flow rates and mechanical forces of the type produced in the machines referred to herein. The term "flash flow" is described in the co-owned U.S. Pat. No. 5,236,734 issued Aug. 17, 1993, U.S. Pat. No. 5,238,696 issued Aug. 24, 1993, and co-pending U.S. application Ser. No. 07/787,254 filed Nov. 4, 1991, and U.S. application Ser. No. 07/893,238, the contents of which are incorporated herein by reference.

Flash flow processing known to the art to date contemplates transformation of feedstock material substantially immediately upon reaching a flow condition whereby the material can move at a subparticle level. Liquiflash processing, however, contemplates the reduction of the feedstock material under conditions of heat and pressure to a condition wherein any resistance to liquid flow, e.g., viscosity which impedes the propensity to form liquid droplets, is eliminated. On a macro scale, this condition appears to provide a liquid or liquiform, which terms are used interchangeably herein.

With liquiflash processing, once the feedstock is reduced to a condition wherein substantially all resistance to liquid flow is removed, shear force is imparted to the flowing feedstock in an amount sufficient to separate individual or discrete particles from the mass. The particles produced by this separation process, referred to herein as discretization, have a size and shape influenced only by the natural mass separation of the flowing feedstock in the presence of the impinging shear force. The particles thus formed are referred to as shearlite particles or particulates. If the impinging force is such that the separation created is that of a continuous stream, discretization has not occurred.

Moreover, the feedstock contemplated for use herein must be capable of undergoing the required transformation without substantial and preferably no significant deterioration of the material present therein.

It has been found that liquiflash conditions and the subsequent shear force imparted thereto in the method of the present invention can be provided by "barrier processing" which is closely akin to flash heat processing as described herein. The flash heat process is a process wherein feedstock can be introduced to a "cotton candy" fabricating type machine. The spinning machine used to achieve a flash heat process can be a cotton candy type machine such as the ECONO FLOSS Model 3017 manufactured by GOLD METAL PRODUCTS COMPANY of Cincinnati, Ohio. Machines useful in the process of the present invention can be found in co-pending U.S. application Ser. No. 954,257 filed Sep. 30, 1992 (incorporated herein by reference), and co-pending U.S. application Ser. No. 08/330,938, filed Oct. 28, 1994, bearing title "Improved Method And Apparatus For Spinning Feedstock Material" (also incorporated herein by reference).

However, in order to implement the liquiflash process as required in the present invention, the flash heat apparatus and process have been modified. In particular, modifications have been made to deliver sufficient energy to the point of transformation of the feedstock, e.g., the barrier of the spinning head, to liquify it instantaneously.

Considerations for successfully carrying out the objects of the present invention reside in the appropriate combination of the following features:

I. spinner head;

II. liquiflash conditions of temperature and centrifugal force;

III. the character and size of the barrier; and

IV. the character of the ambient conditions adjacent the spinner head.

Spinner heads may be adapted to produce shearlite particles. In general, some of the spinner heads presently available can be modified to provide sufficient energy to the feedstock so that in the presence of appropriate centrifugal force the feedstock transforms to liquiform and is processed substantially instantaneously. Gas (air) resistance discretizes the feedstock. Elements identified hereinabove can be adjusted to optimize discretization for a particular feedstock.

In order to deliver sufficient energy to achieve liquiflash conditions, the inventors herein have devised configurations of equipment in which the heat delivered to the barrier is increased. This requirement has been achieved in apparatus disclosed in commonly owned co-pending application Ser. No. 08/330,938, filed Oct. 28, 1994, which has been incorporated herein by reference. For example, the number of individual heaters at the periphery of the spinning head can be increased. Another way of increasing the thermal energy delivered to the feedstock is by providing a tortuous path which retards movement of feedstock through the barrier on the periphery of the spinning head. Those skilled in the art will appreciate that the combination of increasing the delivery of heat and retarding flow of feedstock can be combined by various design features to obtain optimum results in the process and, consequently, the product. As indicated above, it is intended to cover all such variations of control over the delivery of heat and the rate of passage of the feedstock through the barrier as a means of providing liquiflash conditions.

It is preferred that the surface of the spinner head which contacts the feedstock be coated with a low free surface energy substance. For example, a Teflon® based coating will reduce friction between the feedstock and the surface of the spinner head as the feedstock travels towards the processing boundary and is forced thereagainst.

Figure 2A:
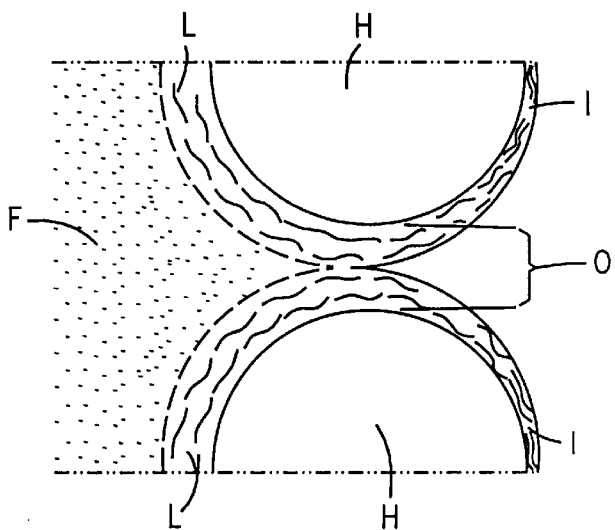
FIGS. 2A, 2B, and 2C are schematic representations of the liquiflash process in accordance with the present invention.
Figure 2B:
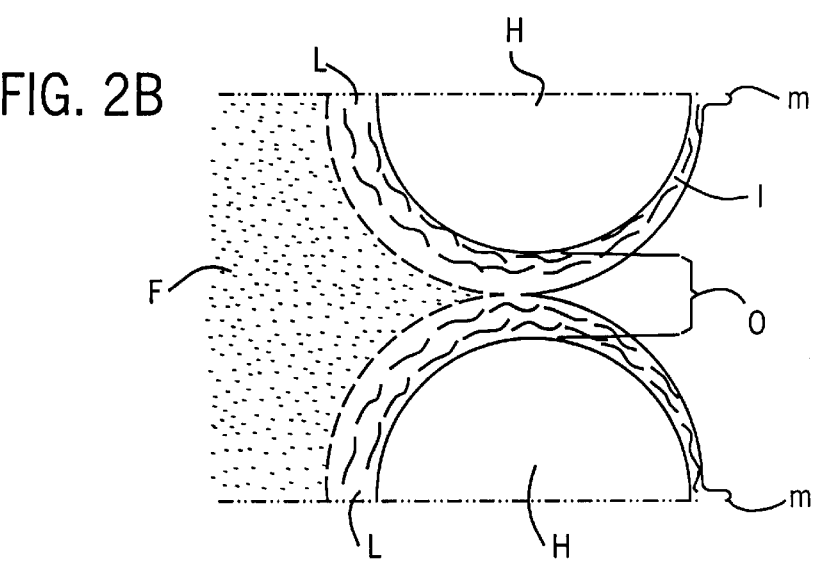
Figure 2C:
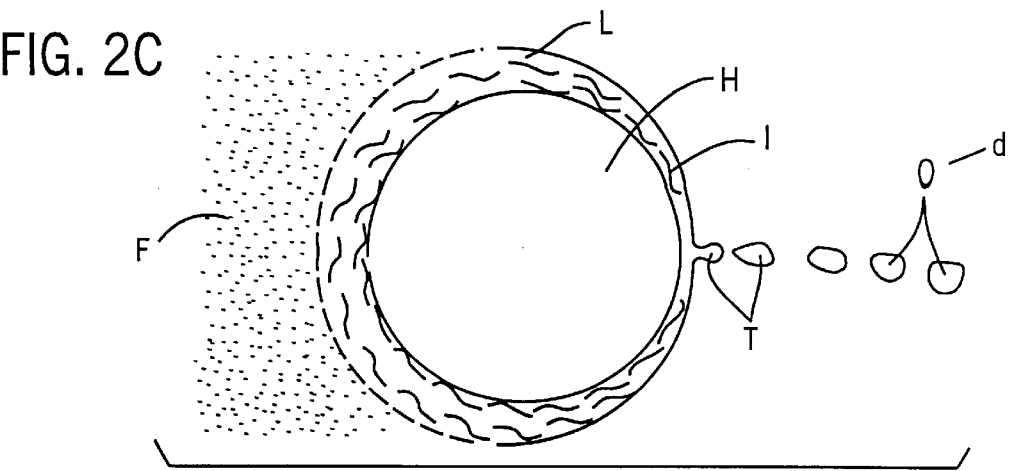

Referring to FIGS. 2A, 2B and 2C, the unique phenomenon of liquiflash is schematically depicted. Centrifugal force created in the spinning head flings the feedstock F to the barrier found at the periphery of the spinning head. Heating elements H provided at the periphery reduce the feedstock to a liquiform condition wherein internal flow becomes unimpeded.

Figure 27:
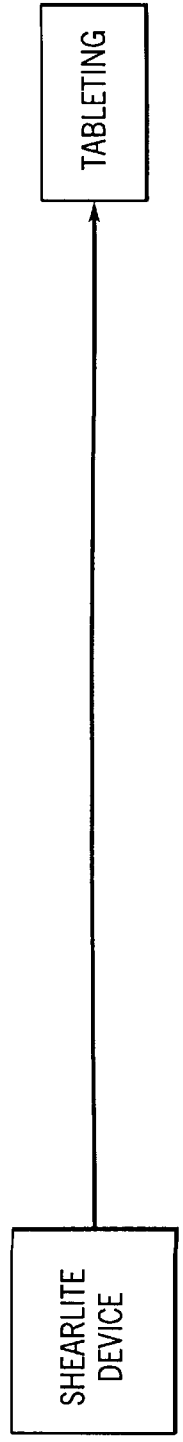
FIG. 27 is a schematic of the process of the present invention.

In this liquiform condition, centrifugal force moves the feedstock through the openings O between heating elements H provided in the peripheral barrier so that the liquid is exposed to shear force provided by the ambient atmosphere found immediately outside the head. It is believed that the flowing feedstock creeps as a layer 1 along the surface of the exterior of the head until a sufficient volume is built up in the Laminar flow whereby a tiny mass m of liquiform feedstock begins to form a generally deformed drop, e.g., a teardrop shape, T, which is met by the atmosphere surrounding the spinning head. The shear force imparted on the teardrop T being formed by the flowing feedstock separates a droplet D as a discrete particle by natural mass separation. Natural mass separation at this point is the combination of weight, internal cohesive intra- and intermolecular forces present in the liquiform feedstock and adhesive forces between the liquiform feedstock and the exterior surface of the spinning head. Inasmuch as there is a continuous flow of feedstock, the teardrops are continuously formed and separated as discrete shearlite particles D. As a consequence of this unique process the discrete particles formed thereby have been found to be highly uniform microspheres, i.e., pearl like spheres having a size of not greater than 500 $\mu$m, and in most cases having a magnitude of between 25 and 300 $\mu$m.

Moreover, the particles produced as a result of this process have been found to have a high degree of purity. Thus, drugs which are processed in the absence of any additives whatsoever have been found to experience a change in morphology which makes them ideal for predictable drug delivery systems. The drug product can also be augmented by processing with additional ingredients which are active or inactive, e.g., delivery ingredients, taste masking ingredients, taste modifiers, dissolution retardants, dissolution expedients, etc.

It is also contemplated that the force required to separate the discrete shearlite particles can be varied by modifying the atmosphere surrounding the spinning head. For example, the apparatus can be operated in a chamber having multiples of atmospheric pressure, or virtually no pressure.

The conditions of liquiflash, i.e. principally temperature and centrifugal force, must be carefully controlled so that on melting to a degree that permits centrifugal force to move the liquiform material to and through the exit orifices, can be accomplished. To obtain this with pure compounds the operator can be guided by its known melting point. With mixtures of materials test melting points can be obtained as a rough guide before starting a run. With little experimentation, heater resistance power can be slowly supplied to a spinner head containing the material to be converted into shearlite microspheres and simultaneously the rate of spinning of the head can be increased until liquiflash conditions are met. The appearance of microspheres of the desired size range verifies that the optimum liquiflash conditions have been met for this particular material. For instance in Example II, set forth below, acetaminophen powder m.p. 169–170.5° C., has been processed in the described apparatus and the heat was progressively increased toward the melting point of the powder while the spinner head increased to about 3600 rpm. Upon melting, and when spheres in the size range of up to 420 $\mu$ appeared, this constituted the optimum liquiflash conditions for this size range shearlites of acetaminophen.

DIRECT TABLETING

In prior art processes, the particles are prepared by different methods. A wet granulation method has been shown in FIG. 26 in comparison to the inventive process shown in FIG. 27. In wet granulation procedures, individual powder particles are coated and then formed into agglomerates which are called granules. Fusion of the ingredients in prior art procedures depends in large part on compression of the ingredients. In the present invention, amalgamation of the ingredients occurs during shearlite formation entirely prior to compression.

Referring to FIG. 27, it can be clearly seen that the inventive process eliminates many steps and/or ingredients required to prepare the feedstock for tableting by the prior art wet granulation method. Moreover, the present invention is also an improvement over traditional direct compression tableting procedures. Direct compression has been known in the art to define a process by which tablets are compressed directly from powder blends of the active ingredient and excipients, such as fillers, disintegrants, and lubricants, which will flow uniformly into a die cavity for tableting by compression. However, traditional direct compression still requires: 1) milling of drugs and excipients; 2) mixing of the ingredients; and 3) tablet compression. See "*Pharmaceutical Dosage Forms,*" Edited by Lieberman, et al., Vol. 2, Pg 112 and 147–161 (1980). The present invention significantly improves the traditional direct compression method by reducing the separate steps of milling and mixing and eliminating the need for excipients to provide adequate flow properties.

Referring to FIG. 27 the process and apparatus of the present invention are schematically depicted. The process include liquiflash processing wherein the active (and/or inactive) ingredients are combined and shearlite particles are formed. These particles are readily flowable and can be transported automatically to and through tablet making machinery without the necessity of excipient(s), and without need for a coating to facilitate flow. Moreover, the shearlite particles can be tableted without the requirement of excipient(s) and/or coatings. Thus, the process of the present invention is simply (1) the forming of shearlite particles followed by (2) direct tableting. "Direct tableting" as used herein means without requirement of excipients and/or coatings, and without required additional process steps and/or flow agents, if so desired. Thus, these other ingredients, and/or steps (such as coatings) may be utilized—not out of necessity, but to engineer or "fine tune" the desired product.

As previously described, it has been advantageously found that excipients in the form of the shearlite particles overcome the disadvantages normally associated with the use of such excipients in a non-shearlite condition. The transformation of an excipient feedstock material to the form of shearlite particles provides the excipient with a shape and size that is compatible with the active shearlite particles. This in turn enables the tableting formulation to maintain a flowability that facilitates direct tableting of the formulation.

Consequently, the mechanical system of the present invention is characterized by a unique combination of apparatus characterized by the absence of devices such as mixers, milling, machines, etc., which are generally included in tablet-making systems. Referring again to FIG. 27, the apparatus of the present invention is schematically depicted as a shearlite device (such as those disclosed herein) and a 28 tablet-making machine which are simply connected for transfer of shearlite particles from the shearlite device to the tablet-making machine. Transfer of shearlite particles can be easily accomplished by uninterrupted transport over a conveyor which connects the shearlite device and the tablet-making machine in FIG. 27. The apparatus of the present invention is defined herein to mean "in the absence of required additional apparatus and/or components." Other apparatus or devices, such as a coating device, may be included to obtain desired result, but these additional devices are not required.

Figure 28B:
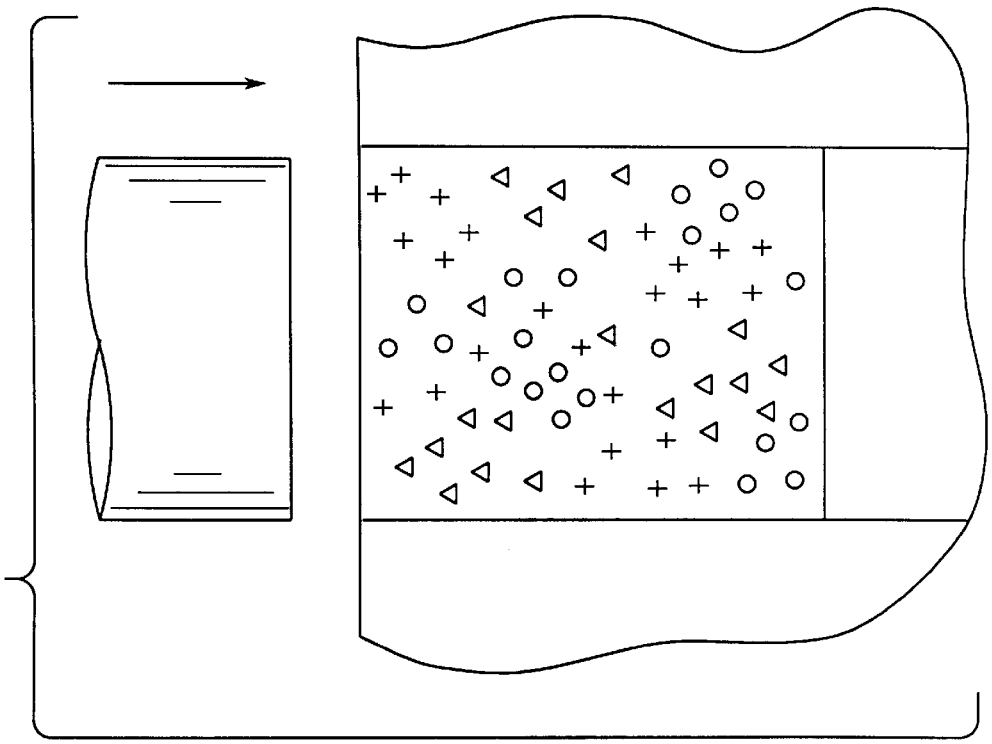
FIGS. 28a and 28b are schematic representations of a loaded precompression tablet mold comparing the inventive procedure and the prior art, respectively.
Figure 28A:
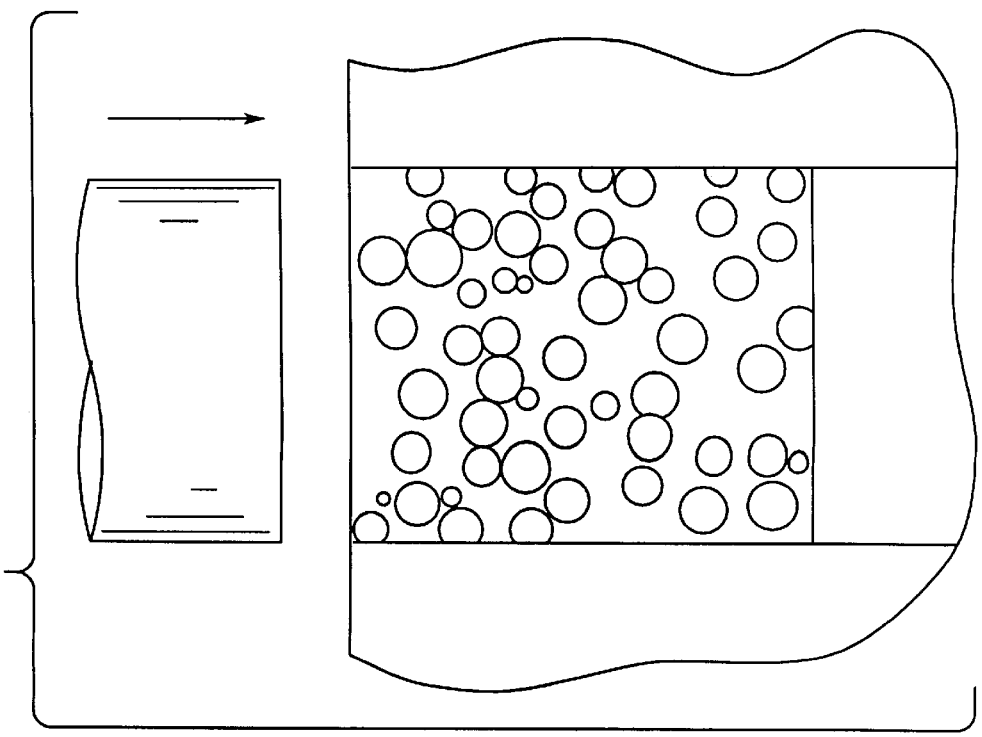
Figure 29A:
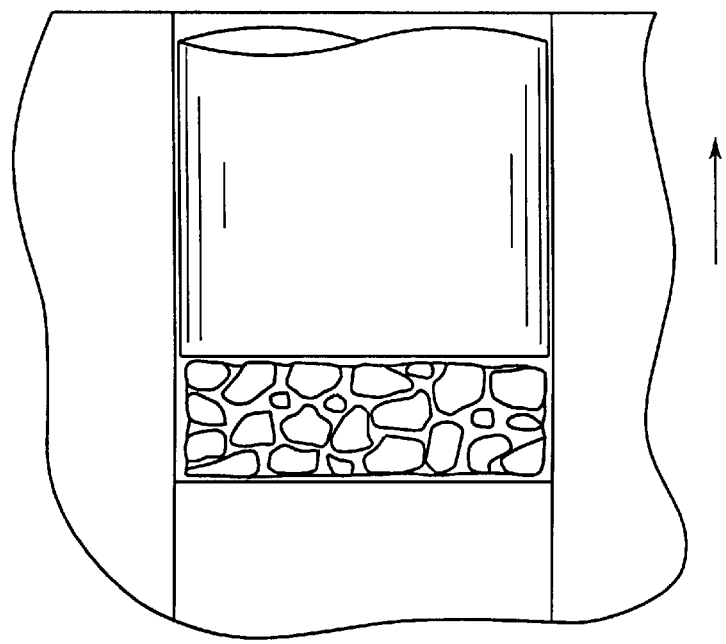
FIGS. 29a and 29b are schematic representations of a loaded tablet mold during compression comparing the inventive procedure and the prior art, respectively.
Figure 29B:
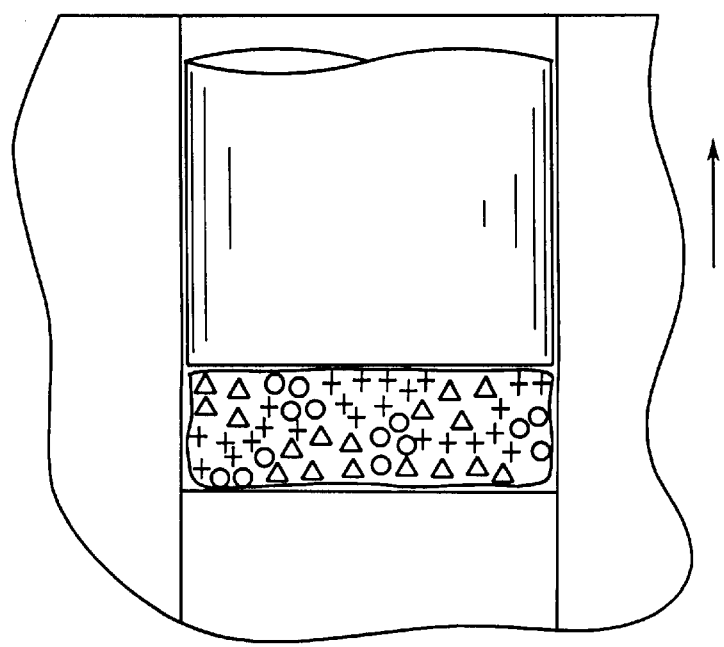

The advantage of the tableting procedure of the present invention are shown schematically in FIGS. 28a, 28b, 29a and 29b. FIGS. 28a and 29a depict respectively, a filled mold cavity (precompression) and the results of compressing the feedstock in accordance with the present invention. FIGS. 28b and 29b depict, respectively, the prior art process of filled mold cavity (precompression) and the results of compressing prior art feedstock.

In particular, in FIG. 28(a), shearlite particles are shown after they have been fed into a compression die. In FIG. 28(b) pre-compression components of a tablet which have not been subjected to shearlite processing are depicted in a die. There are basically three components represented by +'s, Δ's, and o's. Consequently, the ingredients are not part of flowable shearlite particles.

In FIG. 28(a), each of the components are part of the shearlite particles as, for example, an amalgam, while in FIG. 28(b) the components are subject to separation as a result of the feeding mechanisms which direct the particles into the die cavity. The components are not amalgamate and can agglomerate in "clumps of components" as displayed in FIG. 29(b).

FIG. 29(a) shows shearlite particles fused together with all components remaining in amalgam even under compression. Deformation resulting from the force of compression does not force the ingredients out of mixture or cause "clumping." The homogeneity of the mixture is not disturbed as a result of compression.

FIG. 29(b) shows the compression stroke of the prior art process forcing the components into clumps. This phenomenon reduces the homogeneity. Consequently, particles will be together in a non-homogeneous mixture.

SHEARLITE FEEDSTOCK

Feedstock which is contemplated for use herein includes saccharides especially sugars such as sucrose, sugar alcohols such as mannitol, mixtures thereof, and medicaments which can include active agents alone or in combination with other active agents or other ingredients. Quite surprisingly, it has been found saccharides and drugs can be processed without deterioration.

Medicaments which can be used in the present invention are varied. A non-limiting list of active agents which can be included in medicaments herein is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithromobotic drugs, hypnotics, anti-emetics, anti-nauseants, anti-convulsants, neuromuscular drugs, hyper- and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemia drugs and mixtures thereof. Other active ingredients contemplated for use in the present invention are $H_2$-antagonists.

Calcium carbonate ($CaCO_3$), alone or in combination with magnesium hydroxide and/or aluminum hydroxide, can be included with other feedstock used as a carrier. Thus, such antacid ingredients can be used in combination with $H_2$-antagonists, ibuprofen, ketoprofen, etc., which are capable of undergoing liquiflash processing.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate magnesium aluminosilicate, magnesium carbonate, magnesium glycinate, magnesium hydroxide, magnesium oxide, magnesium oxide, magnesium trisilicate, milk solids, aluminum mono-odibasic or mono-dibasic calcium phosphate, tricalcium phosphate, potassium bicarbonate, sodium tartrate, sodium bicarbonate, magnesium aluminosilicates, tartaric acids and salts.

Analgesics include aspirin, acetaminophen, and acetaminophen plus caffeine.

Other preferred drugs or other preferred active ingredients for use in the present invention include antidiarrheals such as immodium AD, antihistamines, antitussives, decongestants, vitamins, and breath fresheners. Also contemplated for use herein are anxiolytics such Xanax; antipsychotics such as Clozaril and Haldol; non-steroidal anti-inflammatories (NSAID's) such as Voltaren and Lodine; antihistamines such as Seldane, Hismanal, Relafen, and Tavist; antiemetics such as Kytril and Cesamet; bronchodilators such as Bentolin, Proventil; antidepressants such a Prozac, Zoloft, and Paxil; antimigraines such as Imigran, ACE-inhibitors such as Vasotec, Capoten and Zestril; anti-Alzheimer agents, such as Nicergoline; and $Ca^H$-Antagonists uch as Procardia, Adalat, and Calan.

The popular $H_2$-antagonists which are contemplated for use in the present invention include cimetidine, ranitidine hydrochloride, famotidine, nizatidine, ebrotidine, mifentidine, roxatidine, pisatidine and aceroxatidine.

Another aspect of the present invention is a new particulate resulting from providing a shearlite particulate substrate in combination of at least one coating. The substrate can either be a non-active ingredient such as a saccharide based material, preferably a sugar such as sucrose, or the substrate can be an active agent, or a combination of active agents. Thus, in one manifestation of this aspect of the invention the substrate can be sugar shearlite particles such as those produced in Example I hereinbelow. Drugs can then be coated thereover either alone or in combination with other types of coating materials. Further coatings can be added as desired. Alternatively, the shearlite particles themselves can be an active ingredient or a combination of active ingredients such as those discussed above with respect to the formation of amalgams. As a result of the narrow size range and the unique and reproducible shape of the particle, coating material can be deposited highly efficiently as very thin even coatings. Consequently, the desired effects such as time-release, flavor enhancement or alteration, can be achieved economically and efficiently.

In one specific embodiment of the present invention, the shearlite particles can be designed to deliver an active ingredient and an antidote. For example, a shearlite particle can be prepared from an active ingredient, an antidote, a non-active ingredient, or a combination of such ingredients. If the particle is an antidote, it can be coated with an active ingredient. If the particle is made from a non-active ingredient, it can be coated with an antidote and subsequently again coated with an active ingredient. In either case a controlled-release coating can be provided thereover and/or interspersed between coatings. Furthermore, another coating such as a muco-adhesive can be deposited to ensure that the active ingredient is delivered to the desired part of the body.

A further preferred embodiment of the present invention includes providing combinations of active ingredients which are designed as a cough and cold treatment. Thus, for example, two or more actives can be included in the feedstock to form an amalgam which can then be directly tableted to form a tablet or coated and then tableted.

In an additional embodiment, two or more combinations of ingredients that prior to the present invention were generally believed to be unstable, interactive or otherwise incompatible may be combined in the feedstock to produce shearlite particles or may be produced separately as shearlite products and coatings and subsequently combined.

"Controlled-release" is used herein to describe a method and composition for making an active ingredient available to the biological system of a host. Controlled-release includes the use of instantaneous release, delayed release, and sustained release. "Instantaneous release" is self-explanatory in that it refers to immediate release to the biosystem of the host. "Delayed release" means the active ingredient is not made available to the host until some time delay after administration. (Dosages are usually administered by oral ingestion in the context of the present invention, although other forms of administration are not precluded from the scope of the present invention). "Sustained Release" generally refers to release of active ingredient whereby the level of active ingredient available to the host is maintained at some level over a period of time. The method of effecting each type of release can be varied.

The patent and scientific literature is replete with various sustained release (SR) methods and formulations. For common methods of obtaining SR systems, see *Sustained and Controlled Release Drug Delivery Systems,* Robinson, Joseph R., Ed., PP 138–171, 1978, Marcel Dekker, Inc. New York, N.Y. Sustained release can be effected by use of coatings, but the present invention also contemplates SR by incorporating the necessary ingredients in the shearlite particles themselves. Coatings which do not detract from the direct tableting aspect of the invention can also be used.

Conventional SR formulations are generally designed to release their actives over an extended period of time, usually 8–24 hours. Conventional SR formulations use waxes or hydrophilic gums to prolong the release of the active ingredients. Conventional waxes and waxy materials used in pharmaceutical formulations are carnauba wax, spermaceti wax, candellila wax, cocoa butter, cetosteryl alcohol, beeswax, partially hydrogenated vegetable oils, ceresin, paraffin, myristyl alcohol, stearyl alcohol, cetylalcohol and stearic acid. They are generally used in amounts of about 10 to about 50% by weight of the total formulation.

Hydrophilic gums have also been known to be reasonably effective as SR carriers for both high-dose and low-dose drugs. Typical hydrophilic gums used as SR carrier materials are acacia, gelatin, tragacanth, veegum, xanthin gum, carboxymethyl cellulose (CMC), hydroxypropl methyl cellulose (HPMC), hydroxypropyl cellulose (HPC) and hydroxyethyl cellulose (HEC). Generally these materials are present in amounts of about 10 to 50% by weight of the final formulation.

Starch USP (potato or corn) can be used as a component in controlled-release formulation. It generally functions in conventional applications as a diluent or as a disintegrant in oral dosage forms. Starch paste is also often used as a binder in these products. Various modified starches, such as carboxymethyl starch currently marketed under the trade name Explotab or Primojel are used as disintegrating agents. The literature discloses that native and modified starches are useful in promoting rapid release of drugs from solid oral dosage forms.

In all controlled release technologies it is desirable to be able to incorporate the active ingredient in its controlled-release pattern in a single dosage unit without deteriorating the active ingredient. Moreover, the dosage unit should be able to deliver the system without interfering with its release pattern.

Polymers are also quite useful in the present invention. Solution coatings and dispersion coatings can be used to coat the shearlite particles. Plasticizers are also normally included in both organic solvent systems and aqueous systems. Some polymers useful for coating include, but are not limited to, the following: methylcellulose (Methocel® A made by Dow Chemical), hydroxypropyl methylcellulose (Methocel® E provided by Dow Chemical or Pharmacoat® provided by Shin Etsu), ethyl cellulose, cellulose acetate, cellulose triacetate, cellulose acetate butyrate, cellulose acetate phthalate, cellulose acetate trimellitate (provided by Eastman Kodak), carboxymethylethyl cellulose (Duodcel®/Freund), hydroxypropyl methylcellulose phthalate, polymethacrylic acid-methacrylic acid copolymer (Type A 1:1 Eudragit® L100; Type B 1:2 Eudragit® S100; and Type C 1:1 Eudragit® L100-55, aqueous dispersion 30% solids, Eudragit® L30D), poly(meth)acryl ester: poly(ethyl acrylate, methyl methacrylate 2:1), Eudragit® NE30D aqueous dispersion 30% solids, polyaminomethacrylate Eudragit® E100, poly(trimethylammonioethyl methacrylate chloride)-ammoniomethacrylate copolymer, Eudragit® RL30D and Eudragit® RS30D.

Plasticizers used in the above solvent plasticizers which may be used in the present invention are as follows: diethyl phthalate, dibutyl phthalate, triethyl citrate, glycerol triacetate, and dibutyl sebaccate.

Aqueous polymeric dispersions useful in the present invention include Eudragit® L30D and RS/RL30D, and NE30D, Aquacoat brand ethyl cellulose, Surelease brand ethyl cellulose, EC brand N-10F ethyl cellulose, Aquateric brand cellulose acetate phthalate, Coateric brand Poly(vinyl acetate phthalate), and Aqoat brand hydroxypropyl methylcellulose acetate succinate. Most of these dispersions are latex, pseudolatex powder or micronized powder mediums.

Plasticizers which can be used include, but are not limited to, the following: propylene glycol, polyethylene glycol (PEG 400), triacetin, polysorbate 80, triethyl citrate, diethyl d-tartrate.

For example, enteric release agents and/or coating broadly include porous cellulose acetate phlatate (provided by Eastman Kodak) in combination with beeswax for blocking its pores. Other combinations include shellac and ethyl cellulose mixtures, and shellac, methyl alcohol and castor oil mixtures. Also an ethylene-vinyl acetate copolymer can be used, such as duPont ELVAX® 40.

Other enteric substances used in or with the present invention are polyacrylate substances bearing many carboxyl groups in their molecules as part of a shearlite amalgam or as a coating. Examples are methacrylic acids-ethyl acrylate copolymers [manufactured by Rhom-Pharma Co. (West Germany) Eudragit® L300D], methacrylic acid-methyl methacrylate copolymer (Eudragit® L or Eudragit®S), hydroxy propyl methyl cellulose phthalate (manufactured by Shin-Etsu Chemical Co., HP-50, HP-55, HP-55S), hydroxypropyl methyl cellulose acetate phthalate (manufactured by Shin-Etsu Chemical Co., AS-LG, AS-LF, AS-MG, AS-MF, AS-HG, AS-HF), carboxymethyl ethyl cellulose [manufactured by Fruent Industry Co. (Japan)], cellulose acetate phthalate, and vinyl methyl ether malic anhydride copolymer [manufactured by GAP Co. (US), AN-139, AN-169].

Preferably, Eudragit® L, Eudragit® S and HP 55 are employed, because they have high contents of carboxyl groups with high safety.

In general, processes known in the art for preparing coated particles can be used. For example, process for preparing particles as disclosed in U.S. Pat. No. 4,971,805 are contemplated for use with the shearlite particles. These processes are incorporated herein by reference and the disclosure set forth in the '805 patent is specifically incorporated herein by reference. See also U.S. Pat. No. 4,948, 622 to Kokubo, et al. which is incorporated herein by reference.

In the Kokubo, et al. '622 patent, the granules, beads and tablets were coated with a dispersion of cellulose ether and then subjected to wax treatment with heating to form a masking layer of wax. It is also contemplated to use waxes as a coating material in the present invention. As previously mentioned waxes include carnauba, beeswax, vegetable waxes, animal waxes (spermaceti) and synthetic wax such as carbowax, e.g., polyether. Also contemplated for use herein includes hydrocarbon waxes such as paraffins and petrolatums. Higher alcohols such as cetyl alcohol and stearyl alcohol, higher fatty acids such as stearic acids, esters of higher fatty acids, fatty acids esters of glycerins such as beaf tallow, lard, hardened soybean oil and hardened castor oil and polyethylene glycols such as PEG-6000 and PEG-20, 000 as well as various commercial products sold under the trade names of Lubri Wax-100 prectrol, which is a mixture of mono-,di-and tripalmitates of glycerin, and the like. These wax materials can be used either singly or as a mixture of two kinds or more according to the need.

The present invention also contemplates the use of fats in the products produced by the present invention. Fats include esters of higher fatty acids, e.g., glycerides of $C_{10-24}$ fatty acids, alcohols, salts, ethers or mixtures thereof. They are classed among the lipids. It is also contemplated that emulsifiers to be included in conjunction with the fats. Emulsifiers include salts of ethanolamines with fatty acids and sulfated fats and oils. Preferred fats include compositions which have mono-,di-or tri-glyceryl esters of long chain of fatty acids. These include but are not limited to stearates, palmitates, laureates, linoleates, oleates, and residues or mixtures thereof having melting points greater than 50° C. U.S. Pat. No. 5,213,810 is directed to compositions including these materials and the '810 reference is hereby incorporated.

The coating process can be effected by spray coating with multiple fats or waxes onto the shearlite particles.

Such coatings can typically be used for taste-masking and controlled-release. As a result of the high uniformity and narrow size distribution, shearlite particles permit the use of substantially less coating materials to produce the intended effect. Thus, with a single complete but thin coat, a high degree of taste-masking and efficient controlled-release can be effected.

In order to illucidate this benefit, an example has been included hereinbelow (Example XII) wherein ibuprofen feedstock is coated and compared to ibuprofen shearlite particles which are coated. The two coated ibuprofen materials were compared for taste. The coated ibuprofen which was not converted to shearlite particles was unacceptable, whereas the processed ibuprofen (subsequently coated) was found to be highly acceptable. Microscopic examination of the unprocessed ibuprofen revealed agglomerated needles of ibuprofen which had varying thicknesses of coating. To the contrary, the shearlite ibuprofen particles displayed a uniform thickness of coating which is ideal for taste-masking and controlled-release.

The present invention contemplates a combination of a low melting fat or wax with an active ingredient which has been transformed to shearlite particles. The material is processed and fed to direct tableting. The fat or wax can also be used as a coating.

In yet another example of the unique advantage provided by the present invention, an antidote material can be transformed to shearlite particles in conjunction with an active ingredient. Both the antidote and the active ingredient may or may not include controlled-release agents to enhance dissolution or to retard dissolution. Any combination of active in antidote can be formulated depending on the need of the practitioner. The active agent can be the shearlite particle while the antidote can be the coating. Additional coatings can be included in a multiple coated product to provide active and antidote. Any combination of these agents suitable for the desired purpose are contemplated as covered by the present invention.

Furthermore, liquiflash processing and products from industrial chemicals which benefit from reduction in dusting and better flow properties are contemplated as part of the present invention. Such industrial chemicals include, but are not limited to, the following: phenol, styrene, butylated hydroxy anisole (BHA), tert butylhydroxy hydroquinone (TBHQ),parabens, hydroquinone, insecticides, herbicides, combinations of insecticides and herbicides, anti-fungals and other agents which suffer from dusting which may cause explosion or may endanger personnel by contact therewith.

As described herein and as illustrated in the following examples, the shearlite particles produced in accordance with the present invention exhibit unexpectedly high flowability. That is, the shearlite particles produced under liquiflash conditions flow easily and evenly under the force of gravity. "Flow easily and evenly" is used to mean that greater than 95%, preferably greater than 98%, and more preferably substantially 100%, of the shearlite particles will flow away from a previously-confining boundary (e.g., a wall of a vessel) without any significant adherence of the particles to the boundary. The particles will also flow away from the boundary without any significant caking or dusting of the particles. More to the point, the particles will flow away from such boundary at a low angle of repose. (The angle of repose defines the angle required to induce flow of the particles from a level "at rest" position.) The particles of the present invention exhibit an angle of repose of less than about 45°, and more preferably less than about 30°.

As will be apparent to those skilled in the art, the ability to convert a non-flowable material into a flowable material improves certain existing applications and processes, and also creates entirely new applications. Thus, any substance capable of being subjected to liquiflash conditions may be processed to provide shearlite particles exhibiting enhanced flowability, without the negative properties commonly associated with multiparticulates such as adherence to boundaries, caking and/or dusting. Moreover, it is contemplated that substances which may not themselves be subjected to liquiflash conditions can be carried by shearlite particles of a compatible material.

According to the present invention, the processing of a substance, e.g., a bio-affecting agent, produces shearlite particles which may thereafter be packaged for subsequent delivery to a recipient, i.e., a patient requiring administration of the bio-affecting agent. Of course, it is contemplated that other substances in addition to bio-affecting agents may be subjected to liquiflash conditions to produce shearlite particles which can thereafter be packaged in suitable containers. These other substances include sucrose, flavor enhancers and various industrial chemicals and the like. In one particularly preferred embodiment, a bio-affecting agent is delivered with and/or carried by shearlite particles of sucrose and/or various flavor enhancers.

As described hereinabove, there are many applications, particularly in the medical field, where the ability to accurately deliver a metered dose of a multiparticulate substance directly to a recipient in the absence of a conventional delivery format is highly desirable. However, the very fact that a substance is reduced to a multiparticulate form has in the past necessitated the need for use of a mechanized delivery device, e.g., a low velocity spray apparatus, because multiparticulates suffer from various physical limitations such as adherence to boundaries, caking and dusting. Thus, it becomes impractical and/or impossible to consistently and accurately deliver a metered dosage of a multiparticulate substance in the absence of a mechanized delivery system. As also discussed above, the use of mechanized delivery devices has certain disadvantages associated therewith including: i) the need to carry the device, ii) size and cost of the device, iii) sterility of the device, iv) accuracy and consistency of delivery of the device, and v) other various inherent limitations.

It has been discovered herein that shearlite particles produced by the subjecting of a bio-affecting agent to liquiflash conditions provide the basis for a novel recipient-dosage delivery system. This delivery system, which entails contact of a metered dose of shearlite particles of a bio-affecting agent and a recipient, e.g., an oral cavity of a host, is produced by the packaging of such shearlite particles in a suitable vessel. This vessel is preferably bifunctional in nature inasmuch as the vessel provides for 1) sterile storage and ready transportation of the packaged particles, and 2) serves to deliver the particle to the recipient (i.e., the particles are delivered directly from the vessel to the recipient without use of a mechanized device or instrument).

As mentioned, a metered dose of shearlite particles is packaged in the vessel. Thereafter, the vessel is opened and the shearlite particles are administered to the recipient, e.g., to the oral cavity of the host. (The term "administer" as used herein is defined as meaning that greater than 95%, preferably greater than 98%, and more preferably substantially 100%, of the shearlite particles are transferred from the vessel to the recipient, this transfer occurring under the force of gravity). In one particular application, the recipient opens the vessel and self-administers the contents thereof, namely, the shearlite particles of bio-affecting agent, by positioning the vessel adjacent to his or her mouth and holding the vessel at an angle of repose whereby the shearlite particles flow from the vessel into the oral cavity of the recipient, whereupon such particles are immediately dissolved and absorbed by the body of the recipient.

The shearlite particles are preferably packaged in a bifunctional vessel. These vessels, as further described hereinbelow, may be produced from various well known manufacturing processes such as injection molding, blow molding and die forming, thus providing a suitable container for sterile storage of the shearlite particles. In this regard, the vessels are readily transportable by the recipient, and are discarded after use. The vessels may be formed from various materials including high density polyethylene, polypropylene, polystyrene, acetyl butyl styrene, propyl acetate and polyethylene terephthalate. In one embodiment, the vessel is preferably formed from a material which is electrically compatible with the shearlite particles inasmuch as contact between the vessel and the shearlite particles does not tend to create and/or retain a static electric charge. Alternatively, the vessel and/or shearlite particles, either before or after packaging of the particles, may be subjected to a static discharge operation.

The vessel is preferably shaped to facilitate delivery of the particles directly from the vessel to the recipient, e.g., the vessel may include a spout and/or lip which directs and thus facilitates the flow of the particles from the vessel. The vessel is preferably sealed closed with a removable closure whereupon removal of the closure by the recipient allows access to the packaged particles for delivery thereof. For example, peel-away backings or covers formed of aluminum foil laminated with polyethylene or mylar film may be adhered around the rim of the vessel following filling of the vessel. Alternatively, various break-away lids or caps can be used to close the vessel. Of course, it is contemplated that other suitable closures may be utilized herein.

In one particularly preferred embodiment, a plurality of vessels are detachably secured to one another thus providing a multi-vessel transportable package of recipient-dosage delivery systems. Such multi-vessel arrangements facilitate the packaging of the product at the manufacturing level, facilitate dispensing of the medicaments, and also facilitate subsequent handling and transportation of the vessels. For example, a multi-vessel arrangement of seven vessels would allow a physician to readily prescribe a week's supply of a particular medicament (assuming the medicament is administered one time per day). In addition, the multi-vessel arrangement allows the recipient to readily transport the medicament.

In another particularly preferred embodiment, at least two adjacent vessels may be arranged so as to allow simultaneous removal of their respective closures for simultaneous delivery of the metered doses contained in such vessels. For example, it may be practical to separately package two different medicaments which are to be simultaneously administered by the recipient. In non-medical applications, it may be desirable to separately package and thereafter simultaneously deliver two industrial chemical or two active ingredient, e.g., a laundry enzyme and a laundry bleach.

As mentioned, the shearlite particles produced under liquiflash conditions exhibit enhanced flowability. More particularly, these shearlite particles are capable of undergoing restricted flow under the force of gravity. Thus, the shearlite particles not only will flow from a generally open-sided vessel, but will flow through a restricted passage, e.g., a funnel-shaped apparatus. This unexpected ability to undergo restricted flow is significant in that it allows the shearlite particles to be packaged in a vessel having an elongated neck or otherwise restricted flow passage leading therefrom which facilitates transfer of the particles from the vessel to the recipient. As described hereinabove, multiparticulate substances which have not been subjected to liqui-flash conditions do not exhibit restricted flow capability, and thus are not suitable for packaging in a restricted flow vessel, or any other vessel for that matter, because the non-processed multiparticulates adhere to the walls of the container, cake, dust and/or generally provide inadequate transfer of the packaged medicament from the vessel to the recipient. The restricted flow capabilities of the shearlite particles of the present invention are also significant in that restricted flow passages are found in various commercial machinery. That is, the ability of the shearlite particles to undergo restricted flow ensures that such particles may be readily transferred through and/or along the machinery.

Figure 17:
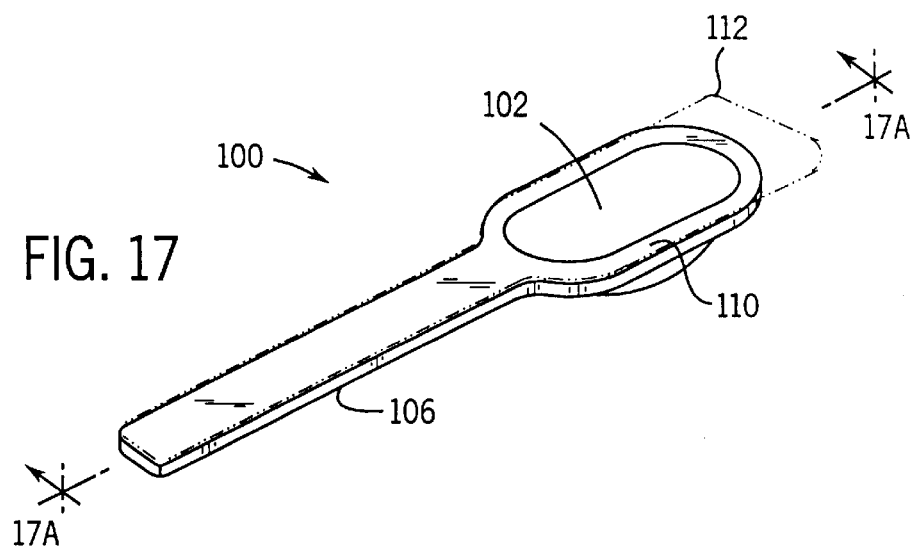
FIG. 17 depicts a spoon-shaped recipient-dosage delivery system.
Figure 17A:
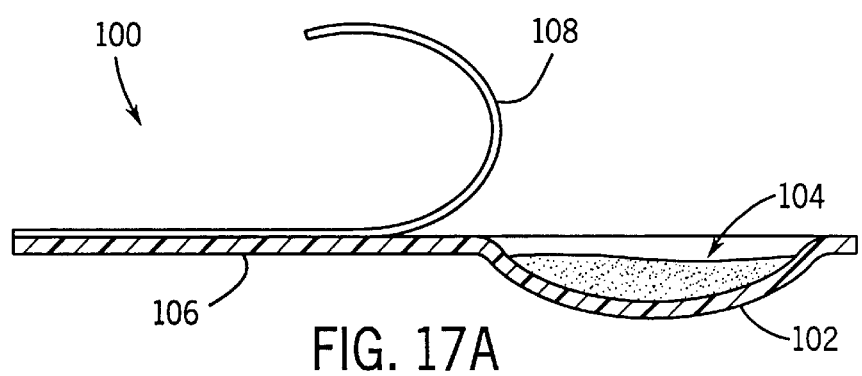
FIG. 17A is a sectional view of the delivery system of FIG. 17.

Referring to FIGS. 17 and 17A, shearlite particles of a bio-affecting agent, e.g., a medicament, may be administered to a recipient via a spoon-shaped vessel 100. Vessel 100 includes a particle-storing bowl 102 sized to receive and hold a metered dose of shearlite particles 104 of a desirable bio-affecting agent and a handle 106 configured to allow manipulation of the vessel by the recipient. The vessel further includes a peel-away backing 108 which is sealingly secured to a rim 110 surrounding bowl 102 following the filling of the bowl with the metered dose of shearlite particles. Backing 108 preferably includes at least one corner tab 112 which allows the recipient to easily peel-away the backing and access the packaged particles.

Figure 18:
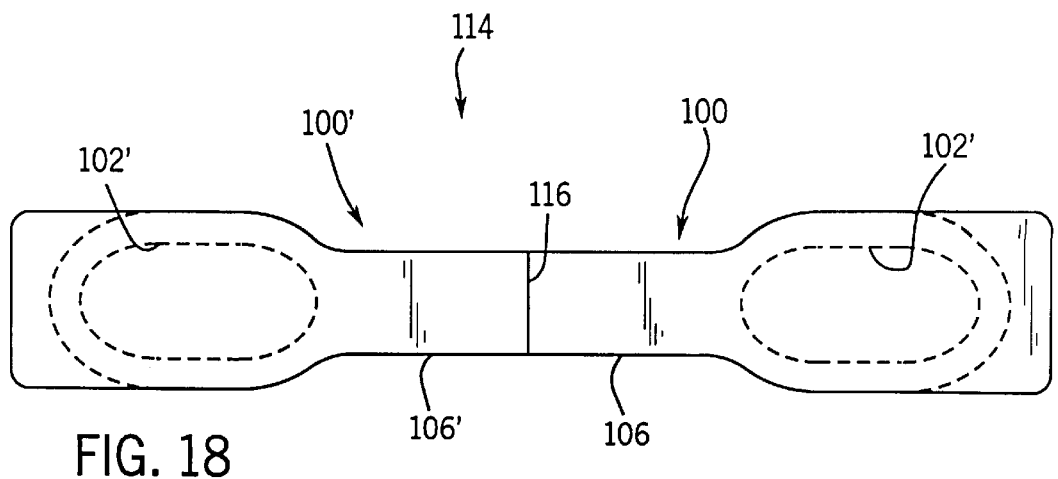
FIG. 18 depicts a multiple-vessel arrangement of recipient-dosage delivery system.

In one preferred embodiment, as shown in FIG. 18, a second vessel, i.e., vessel 100', is fabricated together with vessel 100, thus providing a plurality of interconnected recipient-dose delivery systems, i.e., a multi-vessel transportable package 114. (Of course, it is contemplated herein that any number of vessels may be fabricated together in integral fashion.) Vessel 100' includes a second particle-storing bowl, i.e., bowl 102', affixed to a handle 106'. Handles 106 and 106' are attached along a score line 116 which allows one of the bowls to be readily separated from the multi-vessel arrangement and thereafter discarded once the metered dose of shearlite particles packaged therein has been delivered to the recipient. The multi-vessel transportable package facilitates dispensing and subsequent transportation of the recipient-dosage delivery systems by the recipient. Multi-vessel transportable package 114, which includes two recipient-dosage delivery systems, is particularly suitable for patients who are required to administer two daily dosage of a medicament. An individual self-administers one metered dose of medicament (the first daily administration), breaks off the empty bowl along score line 116, and retains the remaining sealed bowl of medicament for the subsequent second daily administration.

To administer the metered dosage of medicament contained in bowl 102 of vessel 100, the individuals grasps tab 112 of backing 108 and peels away the backing from rim 110, thereby exposing the previously-packaged particles. The individual then empties the contents of the bowl into his or her mouth. Because of the enhanced flowability exhibited by the shearlite particles of the present invention, the particles readily flow from the bowl into the individual's mouth when the vessel is tipped at a suitable angle of repose, typically less than 45°. Moreover, this flow is accomplished without adhering of the particles to the walls of the bowl, caking and/or dusting of the particles and, further, results in the complete emptying of the bowl, that is, substantially 100% of the particles are transferred from the bowl to the recipient.

Figure 19:
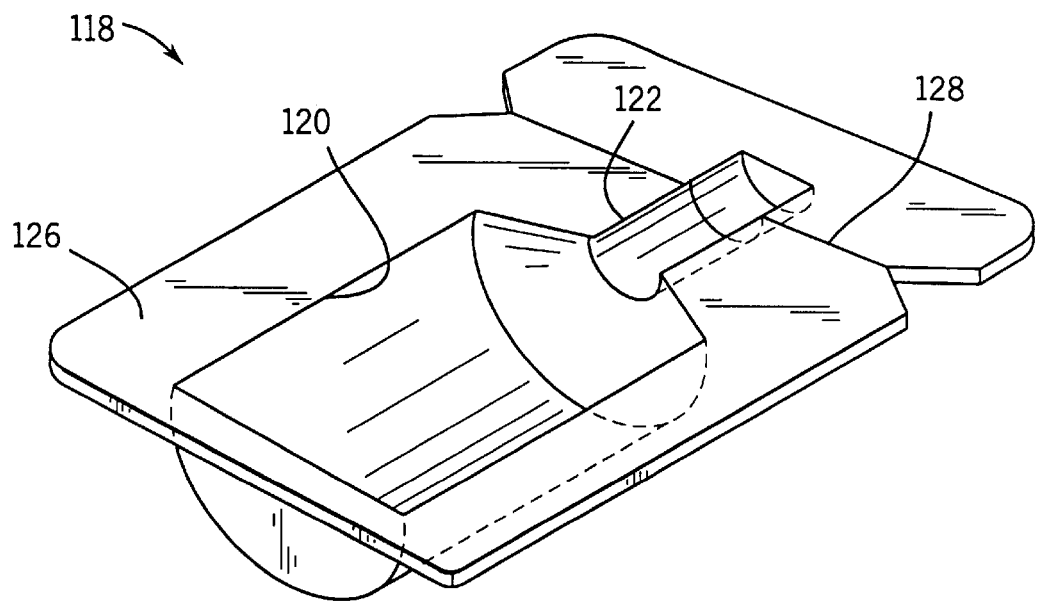
FIG. 19 depicts another embodiment of the recipient-dosage delivery system of the present invention.
Figure 19A:
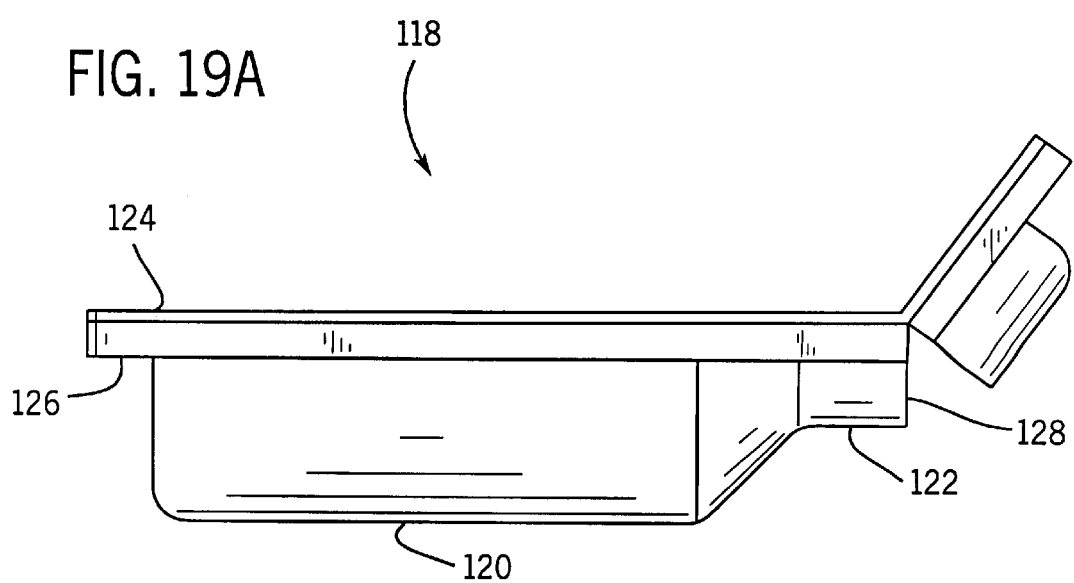
FIG. 19A is an elevational view of the embodiment of FIG. 19 showing the breakaway lid in an open position.

An additional storage and delivery vessel, i.e., vessel 118, is shown in FIGS. 19 and 19A. Vessel 118 includes a flask-shaped particle-storing body 120 having an elongated neck 122 connected thereto. After body 120 is filled with a metered dosage of shearlite particles, the vessel is sealed closed with a backing 124 (shown in FIG. 19A) secured around a rim 126 surrounding the flask-shaped body. The vessel is preferably scored along score line 128, thus allowing a user to readily "break off" the lid and thereby access the packaged particles.

Flask-shaped vessel 118 is particularly suitable for multi-vessel packaging, as shown in FIG. 20. That is, a plurality of interconnected vessels which allow ready separation may be simultaneously fabricated. More particularly, a multi-vessel transportable package 130 includes a plurality of vessels 118 which are detachably secured to one another along score lines 132. As mentioned, the use of multi-vessel packaging facilitates the dispensing and subsequent handling of the delivery systems. For example, the delivery systems may be fabricated in transportable packages of any convenient size, e.g., 7 delivery systems (a one week supply).

An alternative multi-vessel transportable package, i.e., package 134, is shown in FIG. 21. In the disclosed arrangement, the user removes a vessel 136 from the package 134, thus leaving the remaining sealed vessel for subsequent use. Inasmuch as the vessel includes a break-away lid 138 attached to a centrally-disposed tab 140 along score lines 142, the removing of the vessel from the pack results in the opening of the vessel. The user is thus ready, upon removal of the vessel, the deliver to contents of the vessel.

In one particularly preferred embodiment, as shown in FIG. 22, a multi-dosage delivery system 144 is provided (as compared to the single dosage delivery systems discussed above). The multi-dosage delivery system includes a plurality of vessels arranged to allow for simultaneous opening of multiple vessels and subsequent simultaneous delivery thereof. As shown, multi-dosage delivery system 144 includes two particle-storing bodies 146. Each of bodies 146 includes an elongated neck 148 connected thereto. In turn, each neck is sealed closed with a break-away lid 150. The lids are secured to a common tab 152, which upon application of pressure thereto simultaneously breaks off both of the lids, thus allowing the user to simultaneously access and thereafter deliver the shearlite particles packaged in each of the vessels. Applications which may require simultaneous delivery of a plurality of metered dosages include among others various asthma medicaments.

Figure 23:
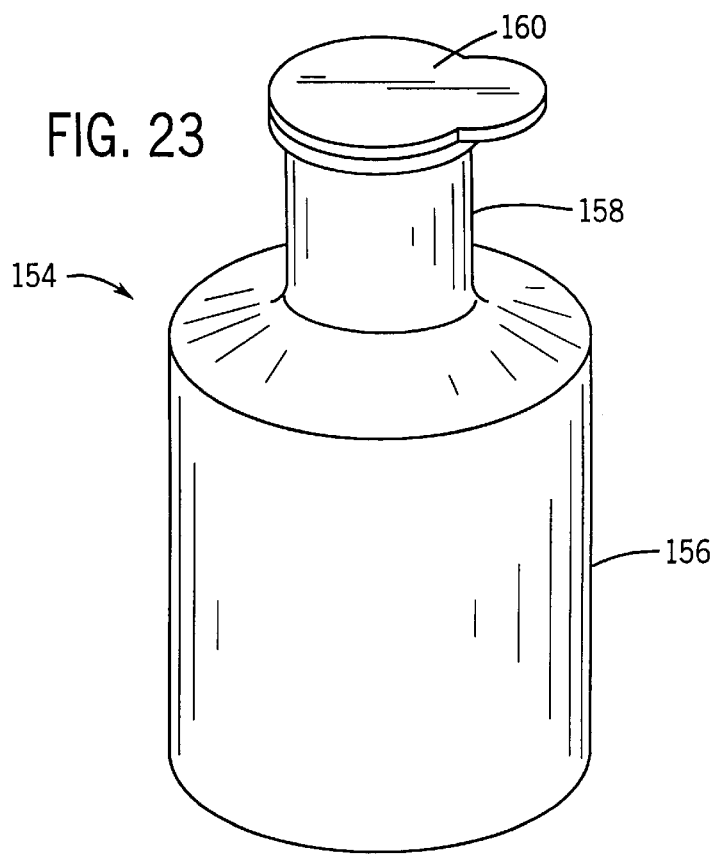
FIG. 23 depicts an alternative vessel for the recipient-dosage delivery system of the present invention.
Figure 23A:
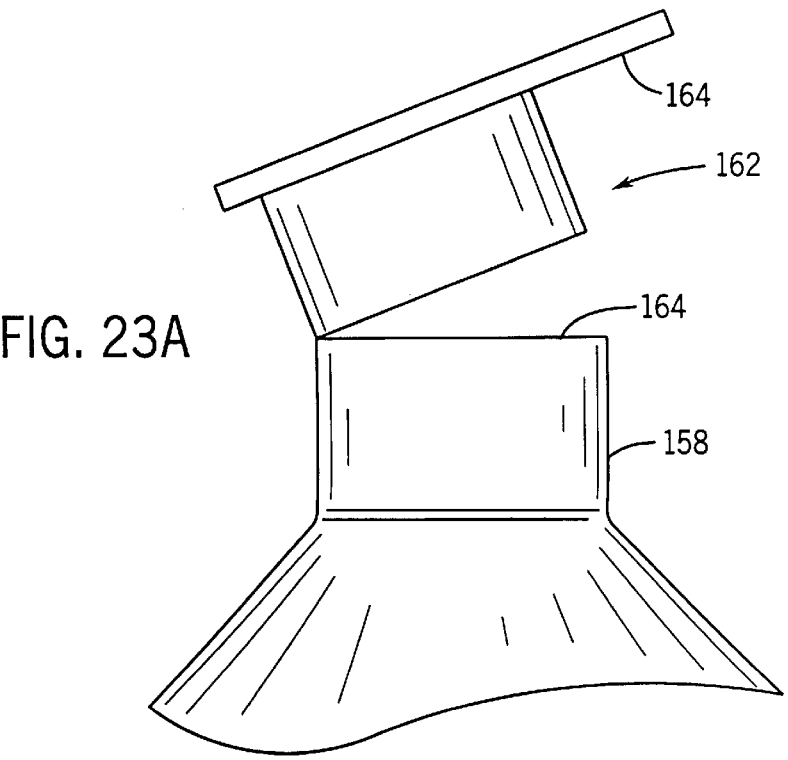
FIG. 23A depicts the vessel of FIG. 23 with a breakaway lid secured thereto.
Figure 26:
FIG. 26 is a schematic of a prior art process.

Referring to FIGS. 23 and 23A, the shearlite particles may be packaged in a discrete vessel, i.e., vessel 154. Vessel 154 includes a particle-storing body 156 having an elongated restricted flow neck 158 connected thereto. The vessel may be sealed with a peel-away cover 160, although alternative closures such as twist-off caps may also be used. One particularly preferred embodiment (shown in FIG. 23A) includes a break-away lid 162 adopted to break off of neck 158 along score line 164 upon application of pressure thereto. Lid 162 preferably includes a finger-engaging tab 164 to facilitate breakage of the lid from the neck. Once vessel 154 has been opened, the recipient thereafter self-administers the shearlite particles by tipping the vessel and allowing the shearlite particles to flow through the neck and into his or her mouth.

In addition, the shearlite particles of the present invention may be packaged in any number of additional manners, including but not limited to a cup-shaped vessel 166 as shown in FIGS. 24 and 24A and an elongate tubular-shaped vessel 168 as shown in FIGS. 25 and 25A.

SHEARLITE DEVICE

Figure 3A:
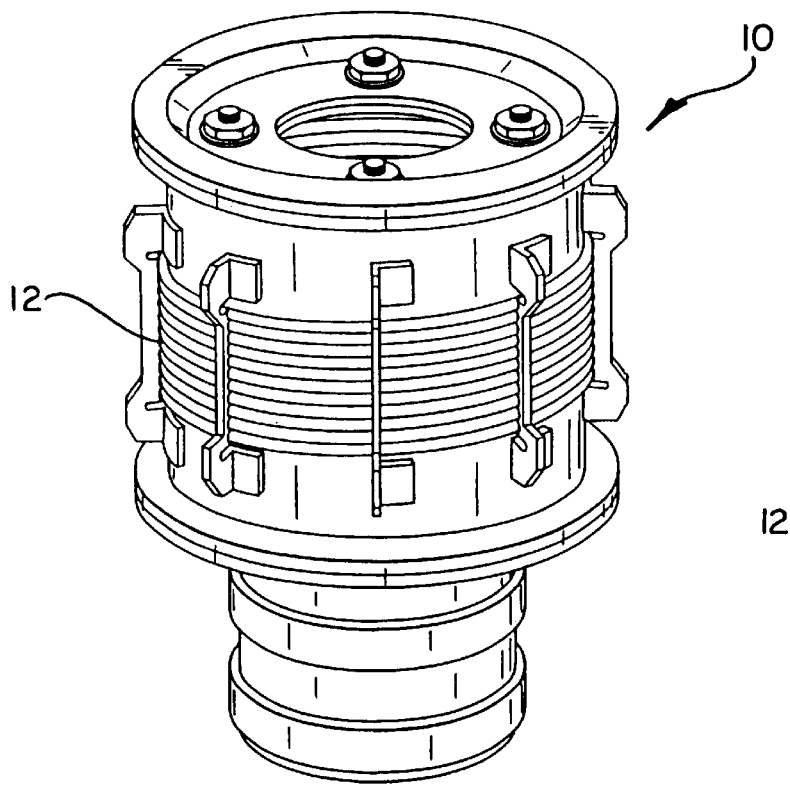
FIGS. 3A, 3B, and 3C depict one shearlite device useful in the present invention.
Figure 3C:
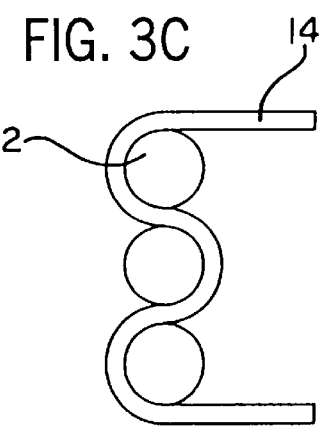
Figure 3B:
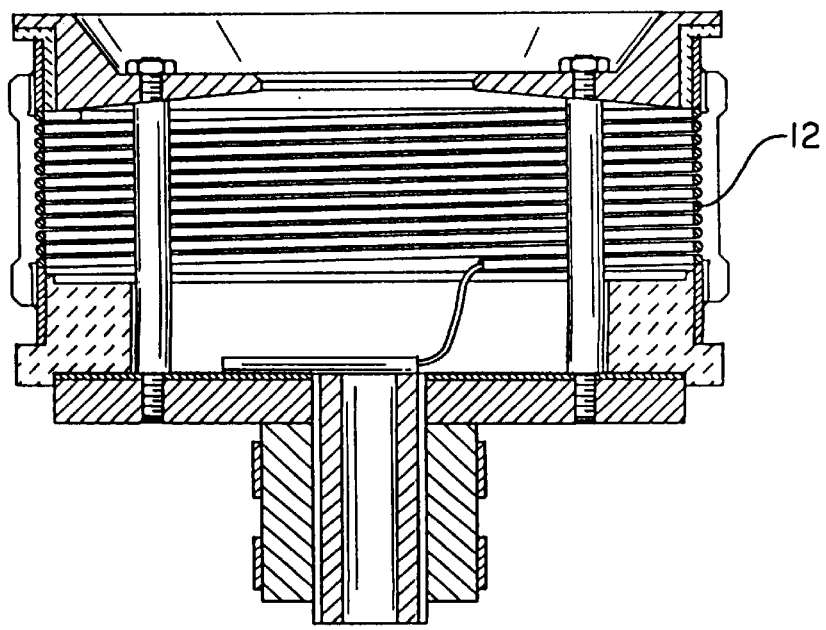

Referring to FIGS. 3A, 3B, and 3C, a first spinning head has been shown which can be used in the liquiflash process. The assembled head 10 is depicted in FIG. 3A. This head is of the type which is disclosed in U.S. Pat. No. 07/954,257 filed Sep. 30, 1992 and its continuation in part application bearing Ser. No. 08/192,133 filed Feb. 4, 1994 (both of which are incorporated herein by reference).

Referring to the spinning head shown in FIG. 3A, a heating element(s) are depicted as continuous cable 12 which is helically wound thereabout. The cable heating element can consist of several cables or even just one cable which is continuously wound around the periphery of the head 10. The embodiments disclosed in the two (2) applications referred to above have certain characteristics, such as slits, etc., for flash flow processing.

In the present invention, however, the small openings in the head are achieved by lacing a shim 14 between the coils of the heater 10. FIG. 3C is a diagrammatic sketch of this embodiment. The shim material 14 is preferably a very thin strip of food grade metal such as stainless steel. The thickness of the shim can be from 0.001 to 0.006 inch in thickness. Preferably, the thickness of the shim is about 0.002 inch. The shim can be about 0.100 inches wide. The lacing can be provided at several locations around the perimeter of the head. Furthermore, teflon coating insulators can be provided in conjunction with the heating cable in order to reduce the friction of the surface of the heating elements.

Figure 4A:
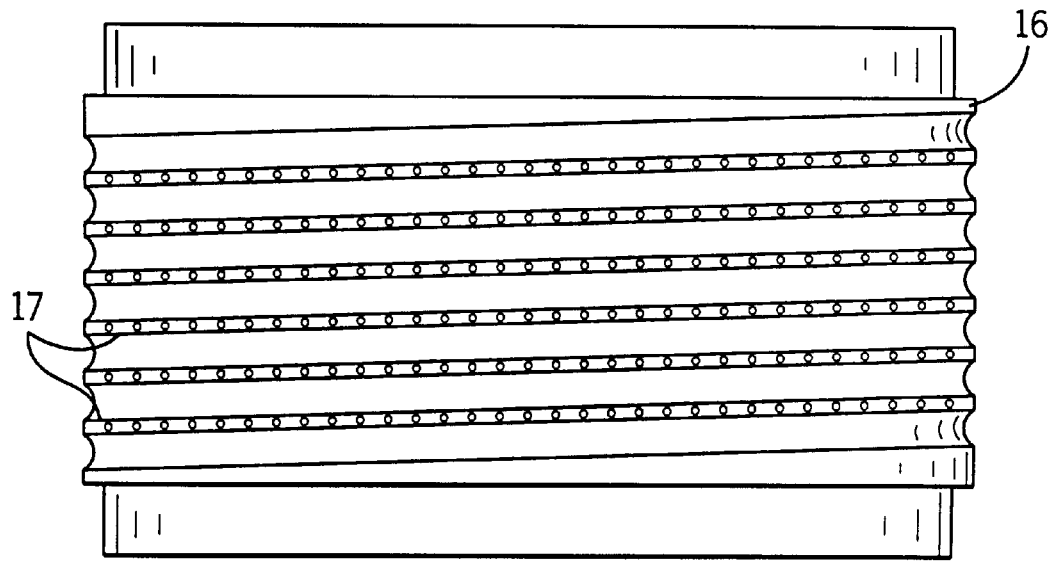
FIGS. 4A, 4B, and 4C depict a second shearlite device which has been used in the present invention.
Figure 4B:
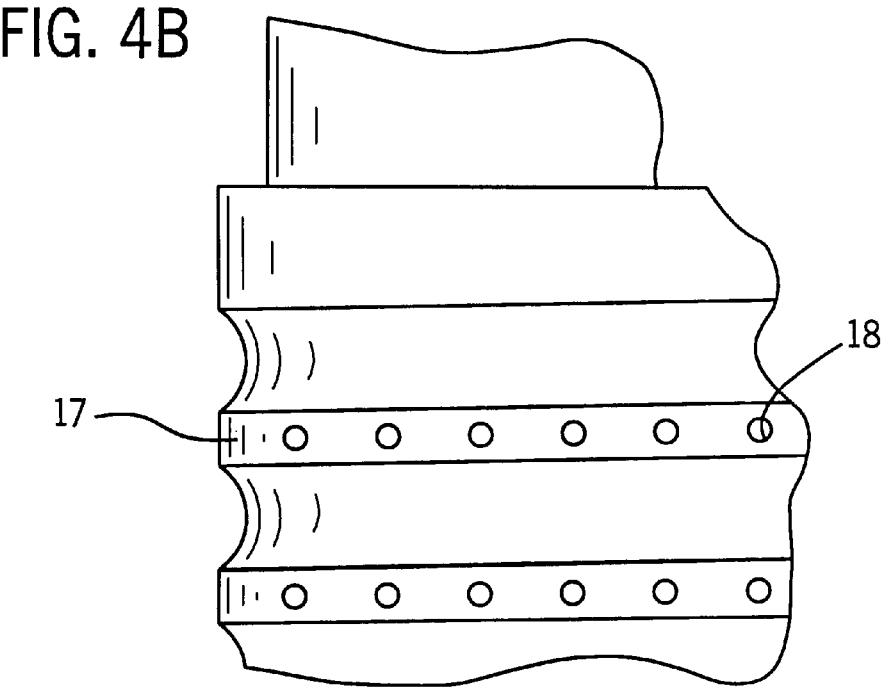
Figure 4C:
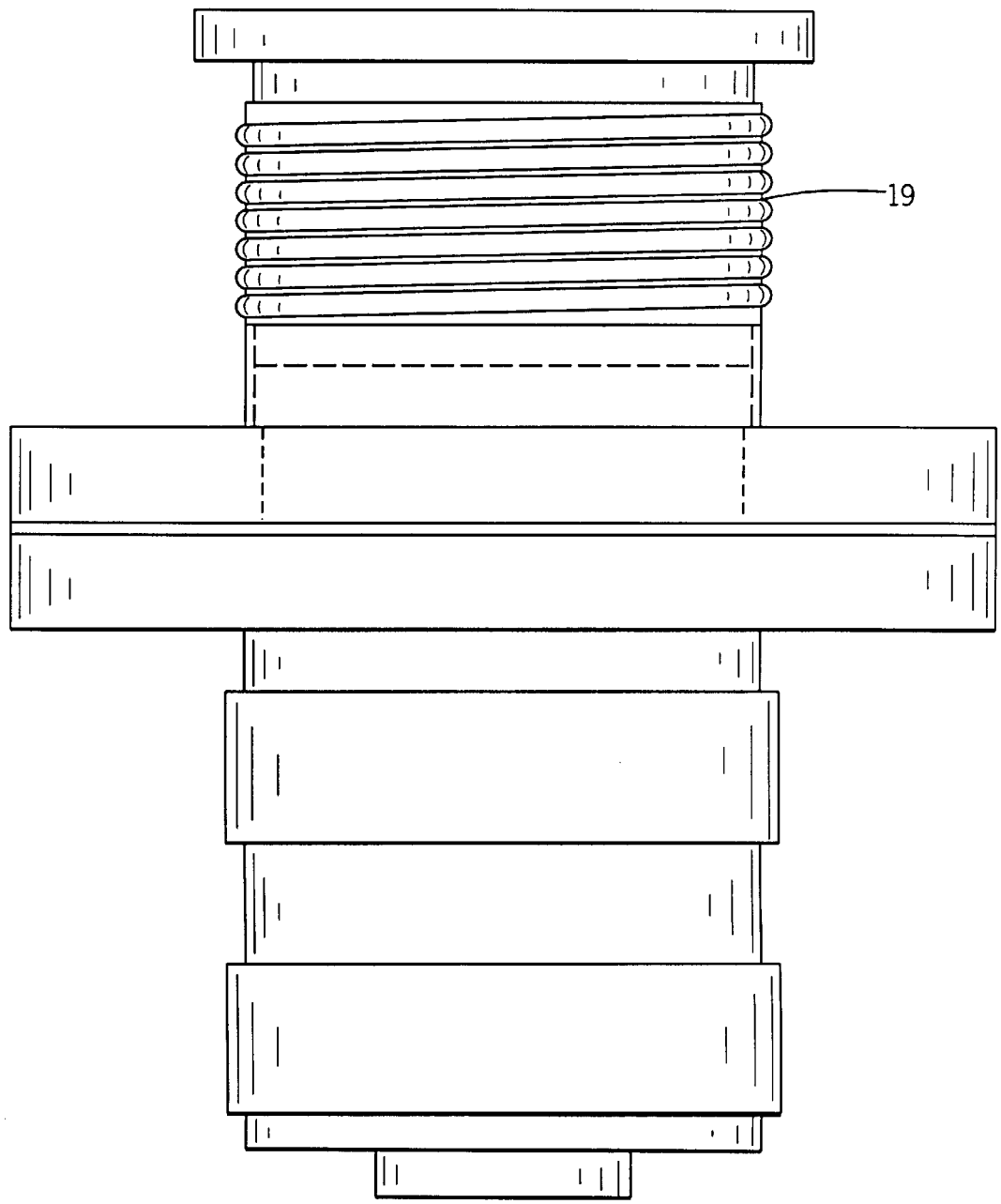

Yet another embodiment of apparatus which can be used in the present invention is shown in FIGS. 4A, 4B, and 4C. The apparatus of the type used herein has been disclosed in U.S. application Ser. No. 08/226,234 filed Jun. 27, 1994 (which is incorporated herein by reference).

Referring to FIGS. 4A–C, a spinning head silhouette 16 is shown having spaced apart protruding ribs 17 in which tiny openings have been drilled. Preferably the openings are on the order of 0.020 inches in diameter. Referring to FIG. 4B, a cut-away section of the head of FIG. 4A is shown with the holes 18 in the raised ribs 17. A heating element 19 can then be wound around the outside surface of the head 16 in order to provide heat sufficient to melt the feedstock on the interior surface of the spinning head.

The spacing and configuration of the holes can be adjusted by those skilled in the art to achieve the results which are desired. A discussion of this has been fully set forth in the above-identified pending U.S. application. Other variations of this embodiment including size of holes, spacing between the holes, and shape of the openings through the head can be varied depending upon the application. It has also been found that the openings in the configuration shown in FIGS. 4A–C are ideally provided by drilling with a laser beam.

Figure 5A:
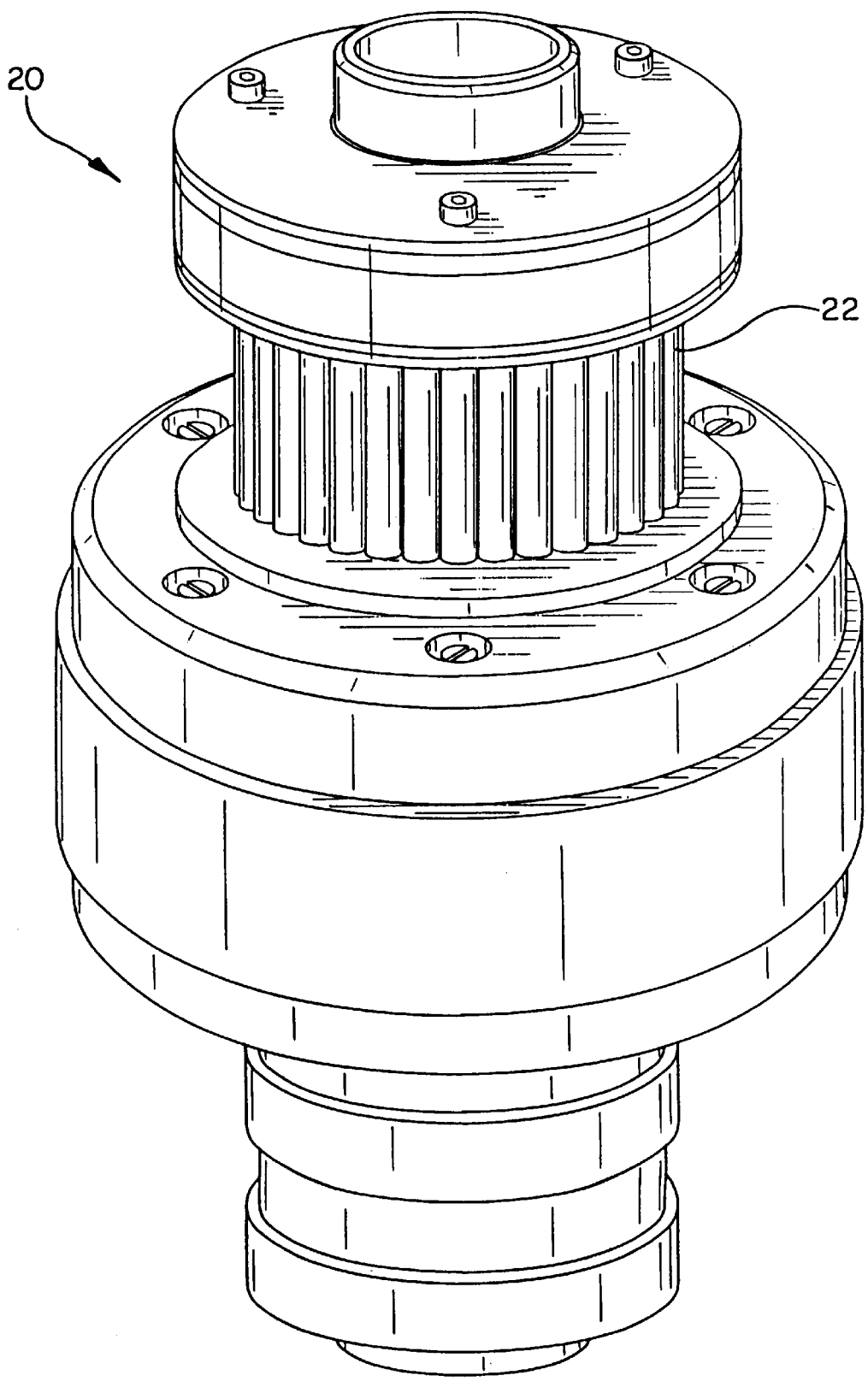
FIGS. 5A, 5B, and 5C depict a third shearlite device used in the process of the present invention.
Figure 5B:
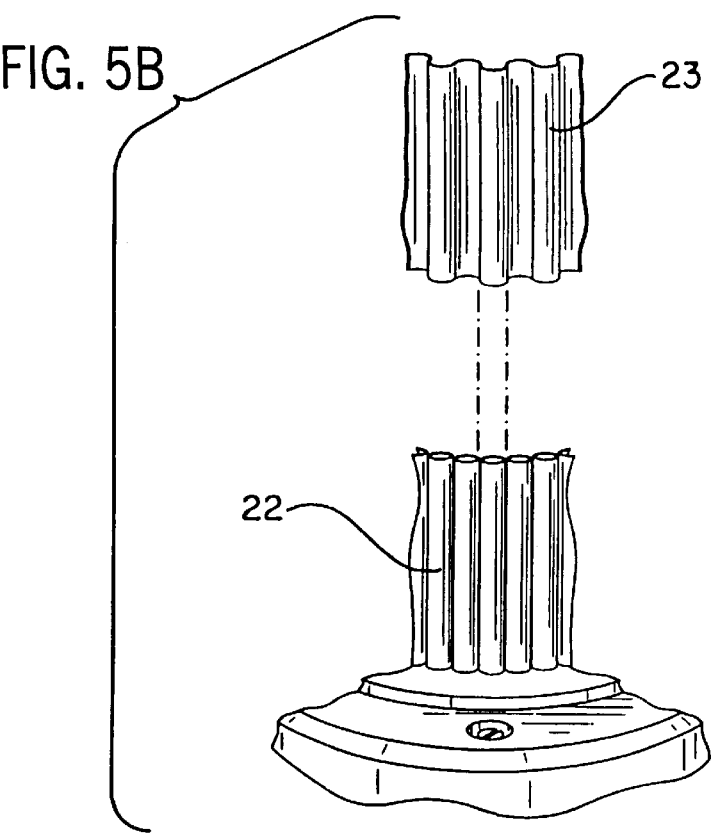
Figure 5C:
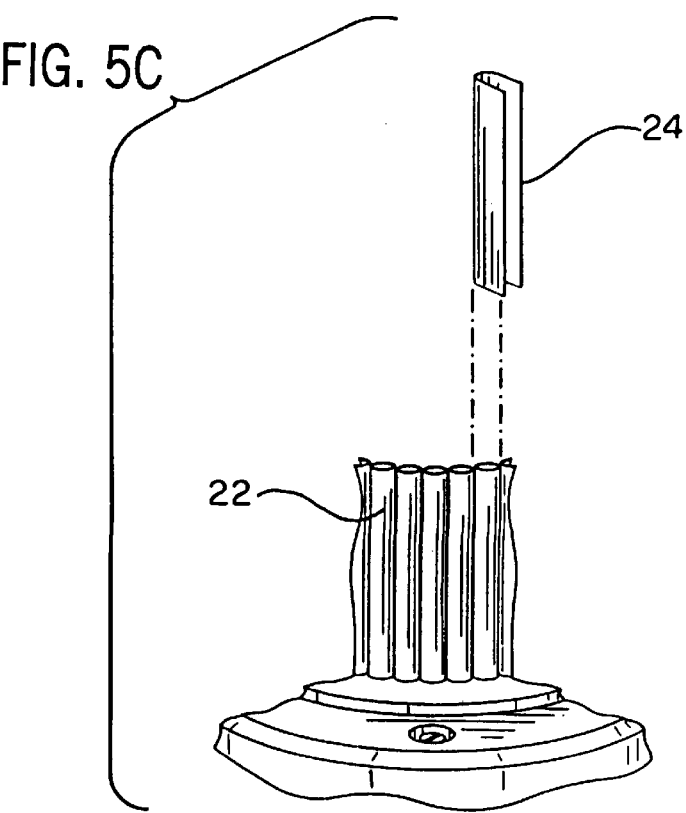

Yet another apparatus used in the present process is shown in FIGS. 5A, 5B, and 5C. The apparatus shown in these figures is of the type disclosed in commonly owned copending U.S. application Ser. No. 08/330,938, filed Oct. 28, 1994, and having the title "Improved Method and Apparatus For Spinning Feedstock Material." In FIG. 5A, a spinning head 20 is shown with upright closely spaced heating elements 22. In a preferred embodiment, electrical current can be provided to each element. In this way, a high degree of control can be maintained over the heat supplied to the processing barrier. Furthermore, the elements can be spaced as closely together as possible in order to provide a restricted passageway for passage of liquiform material.

In another preferred embodiment as shown in FIG. 5B, a continuous screen can be interwoven between the heating elements in order to affect the size of openings through the barrier and also to provide a barrier with relief which enhances drop formation. It has been found that screens with 60 mesh and 30 mesh can be used. The actual opening size, e.g., mesh, can be selected by the artisan.

In yet another embodiment, each heating element 22 can be individually provided with a shim 24 which further reduce the size between the heating elements. As a result of using the shims, opening sizes on the order of 0.005–0.007 inch can be reduced to openings on the order of 0.002 inch.

In each of the embodiments, the head has a diameter of about 3 inches. The apparatus in the present invention has currently been run at a rotational velocity in the area from around 3,000–5,000 rpm. The actual speed can vary from as low as 500 rpm to as great as 100,000 rpm. It is contemplated that many commercial embodiments will be run in the area of 35,000–40,000 rpm. Once again, the size of the head and the rotational speed of the head will depend on the desired results, and other factors such as the size and nature of the feedstock, and the ambient atmosphere adjacent to the spinning head.

Figure 6B:
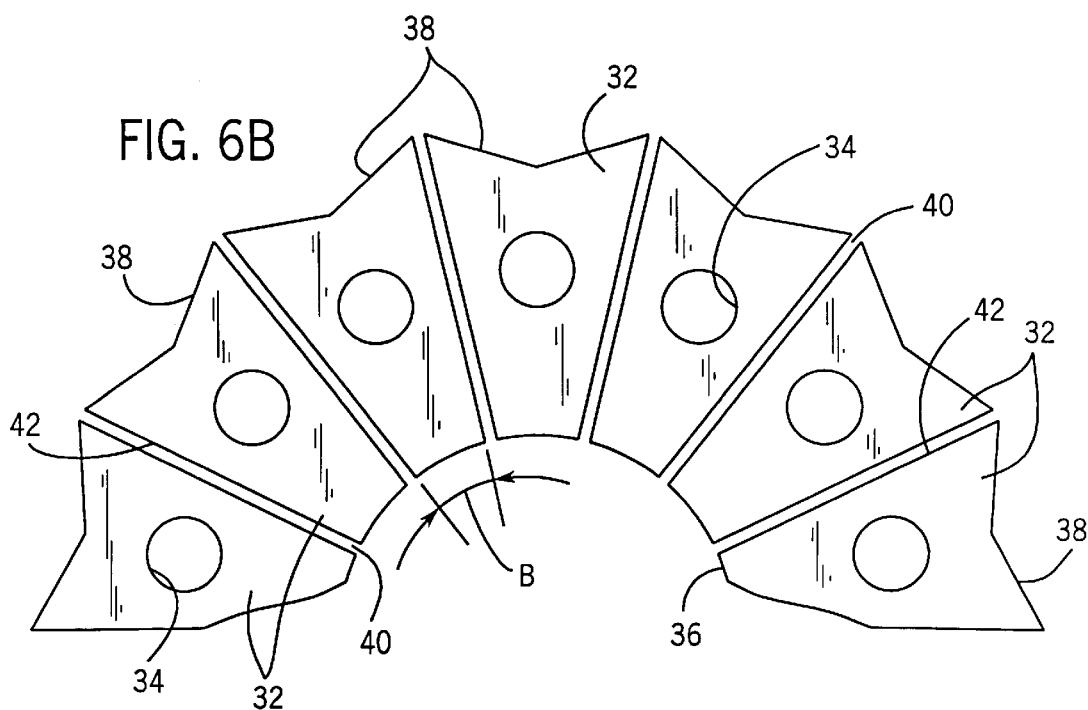

Referring to FIGS. 6A and 6B, a further modification of spinner head 10, particular useful with pharmaceutical product, as described above, is shown. Spinner head 10 is modified in a manner similar to the embodiment set forth above wherein a number of tubular heating elements 30 have been provided. However, in order to narrow the opening through which feedstock materials expelled, this embodiment employs individual modular blocks 32 which fit over heating elements 30.

Each modular block 32 includes a metallic heat conductive body having a central cylindrical passage 34 therethrough which is constructed and arranged to accommodate individual tubular heating elements 30. Each modular block 30 also has a generally trapezoidal cross-section having a smaller wall 36 which faces inwardly toward the feedstock chamber and an opposite wider outer wall 38. In a preferred form, the outer wall 38 may include angular surface 39, which provides for longer opposed side walls 40 and 42 without increasing the mass of modular blocks 30. The modular blocks 30 can be slipped over tubular heating elements 30. As shown in FIG. 6B, walls 40 and 42 form radially directed slots between adjacent modular blocks 32 through which feedstock material may be processed and expelled in a manner similar to that explained above with respect to the previous embodiments. The radially directed slots can be adjusted to alter the size of the passage through which the feedstock material is expelled.

As shown in FIG. 6B, blocks 32 can be rotated about tubular heating element 30 (see arrows B) to cant or twist the blocks, thereby changing the spacing and/or direction of the slots. The rotation of blocks 32 can be accomplished individually or may be rotated in unison with an appropriate mechanism (not shown). With such a mechanism, modular blocks 32 may move in a manner similar to an iris diaphragm of a camera to increase or decrease the size of the passage defined by the slots.

Figure 7:
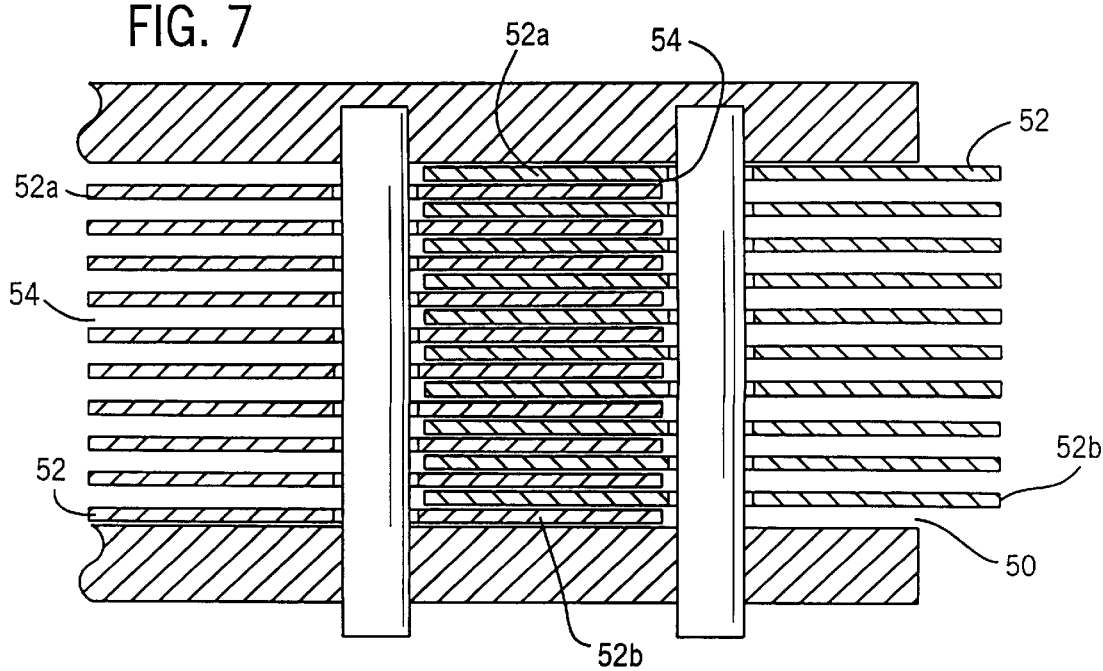
FIG. 7 depicts an additional shearlite device used in the present invention.

A further construction of block 50 is shown in FIG. 7, where transverse slots are formed. Modular block 50 can include a body formed to have a series of vertically spaced horizontally extending fins 52. Modular block 50 can be constructed so that one set of fins 52a interleave with an adjacent set of fins 52b of an adjacent modular block 50. In this manner a series of vertically spaced transverse slots 54 are formed through which feedstock material may be processed.

Referring now to FIG. 8, still further embodiment of the spinner head of the present invention is shown. Spinner head 55 of the present invention includes a generally circumferential array 55a of horizontally disposed tubular heating elements 56. A set of vertically spaced horizontally extending heating elements 56 can be positioned between an adjacent pair of vertically extending support elements 57. Each of support elements 57 can be positioned and spaced in circumferential fashion about base 55b. Appropriately, configured retaining openings 55c are provided to accommodate support elements 57.

Horizontally disposed tubular heating elements 56 can be of similar construction to tubular elements previously described hereinabove. All or selected ones of tubular heating elements 56 may be individually powered in accordance with the present invention. It is also contemplated that vertical support elements 57 in additional to supporting horizontally extending tubular heating elements 56 may also provide a common power bus to energize the individual tubular heating elements. Vertical support elements 57 include appropriate openings spaced therealong which accommodate the ends of tubular heating elements 56 therein in an interference fit such that the securement between the tubular heating elements 56 and the vertical support elements 57 is achieved under both ambient and running temperatures. The space is between adjacent horizontally disposed tubular heating elements 56 can be adjusted to vary the openings through which feedstock material is processed.

It is further contemplated that tubular heating elements of uniform size and configuration or of differing size and configuration may be employed within the same spinner head. An arrangement of the same or different size tubular heating elements allows the spinner head to be statically and/or diametrically balanced. As described above with respect to the spinner head having vertically disposed tubular heating elements, horizontally positioned tubular heating elements 56 of the present embodiment can be canted are skewed with respect to support elements 57.

Furthermore, even though FIG. 8 shows one circumferential arrangement of array 55a, other arrangements are also within the contemplation of the present invention. Further, plural concentric sets of arrays of horizontally disposed tubular heating elements are within the contemplation of the present invention.

The embodiment shown in FIG. 8 also has particular utility with respect to pharmaceutical products since the individual tubular heating elements 56 supported between a common bus such as vertical support element 57 can be easily removed for cleaning as necessary in the processing of pharmaceutical products.

Those skilled in the art will appreciate that other factors will directly affect the size and shape of the apparatus, and is intended to include all variations that come within the spirit of the invention as defined in the appended claims.

EXAMPLES

Example I

Sucrose Spheres

In the first example, the apparatus disclosed in FIG. 5A was used in the liquiflash process for transforming sucrose. The opening between adjacent heating elements in the apparatus shown in FIG. 5A was 0.20 inches. The head was spun at 3600 rpm as it was heated to 180° C.

As the temperature reached its peak, sucrose was subjected to liquiflash conditions and exited the spinning head as a result of centrifugal force. Solid spheres (i.e., shearlite particles) were formed which ranged in size from about 100–200 μm in diameter. The very unique and uniform size distribution is clearly shown in the photomicrograph herein at FIG. 9. The magnification of Figure is 50.

Figure 9:
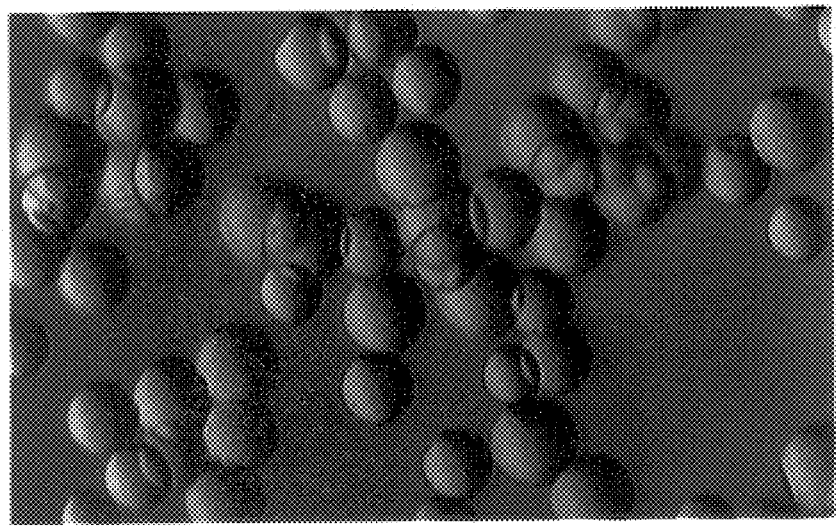
FIG. 9 is a photomicrograph at 50×magnification of a sucrose product prepared in accordance with the present invention.

In this particular case, the size of the rock candy prevented passage through the barrier and provided delay at the barrier sufficient to cause sucrose to transform to liquiform and be instantaneously processed to the highly uniform microspheres depicted in FIG. 9. These spheres are substantially solid throughout, and can be used in a variety of ways, such as a substrate for depositing of material thereon.

It should be noted that microspheres having a diameter of from about 5–50 μm and preferably around 25 μm are excellent for use in conjunction with chocolate. Very small and highly uniform microspheres enable the practitioner to provide a highly acceptable low fat chocolate product. Thus, the processing of sucrose, such as in the form of rock sugar, could be used quite effectively to provide an ingredient for the preparation of a chocolate product.

Example II

Acetaminophen Spheres

In this example, acetaminophen was processed using the apparatus showed in FIG. 5B wherein the screen was a 60 mesh screen positioned in serpentine fashion between adjacent heating elements. Acetaminophen powder (melting point 169–170.5 ° C.) was fed to a spinning head run at about 3600 rpm. While the feedstock was subjected to centrifugal force, the temperature was raised until the acetaminophen powder was reduced to liquiform. The force generated by the spinning head expelled acetaminophen out of the spinner head, and impelled it through the 60 mesh screen. The product was permitted to free fall below the head a distance of from about 6 to 8 feet.

During this transition, fine spheres all of which were less than about 420 μm, were formed. 4.33 kilograms of this material was passed through a 40 mesh screen and 1.39 kilogram of the product was retained.

Figure 1B:
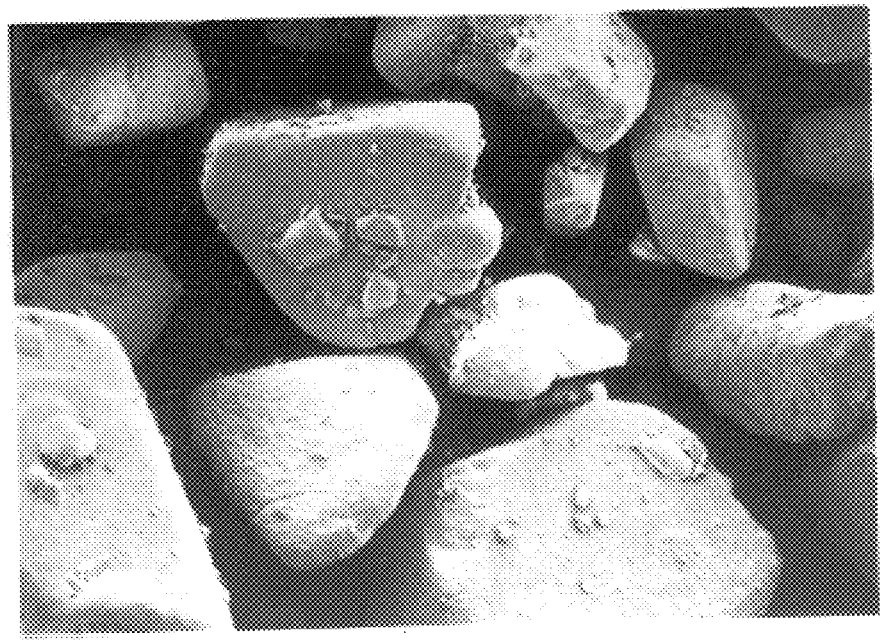
Figure 1C:
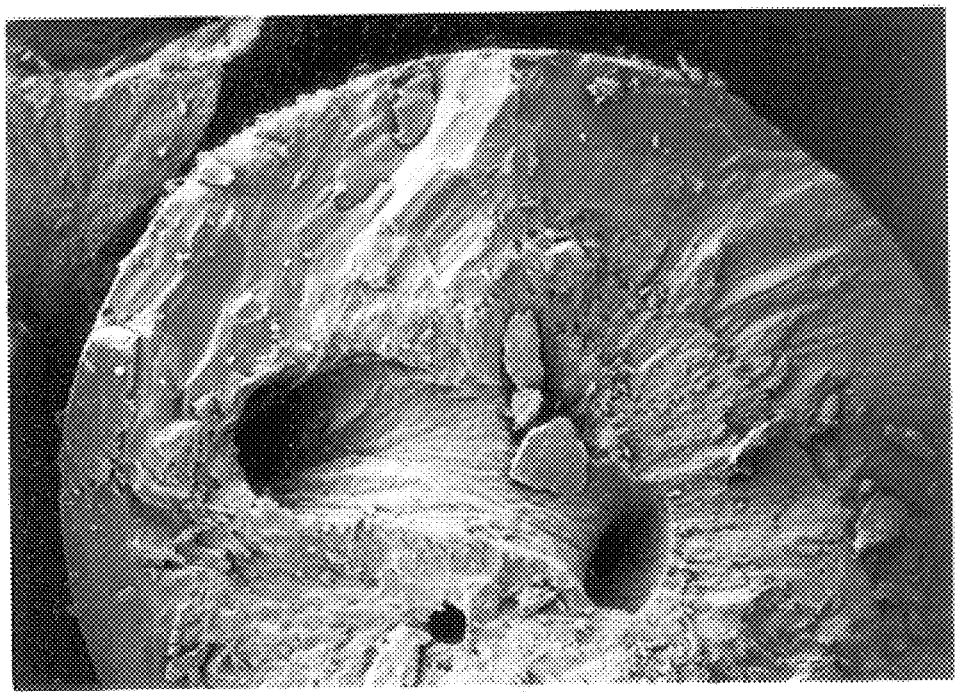
FIG. 1C is a photomicrograph at 500×magnification of a cross-section of a sphere shown in FIG. 1A.

The feedstock, and product resulting from this experiment have been shown herein in FIGS. 1A, 1B, and 1C. In FIG. 1B, a photomicrograph of the feedstock is shown at 125× magnification. After processing, the resulting product was collected and a photomicrograph taken which is shown in FIG. 1A. As can be seen, a highly consistent and very uniform spherical product was produced. Comparing the product shown in FIG. 1A to the feedstock at FIG. 1B, the skilled artisan can readily ascertain the enhanced predictability and processability which is provided as a result of the present invention. FIG. 1C is a photomicrograph at 500× magnification taken of a cross section of a sphere shown in FIG. 1A. As can be seen, the sphere is substantially solid throughout having virtually no openings or voids therein.

Once again, this product enables the artisan to provide a highly efficient drug product which can be used readily in delivery systems.

Example III

Coated Acetaminophen Spheres

Acetaminophen spheres prepared in Example II, were then coated with a formula consisting of 2.5% Eudragit® E100, 7.5% ethocel in a solvent having acetone and methanol in 8 to 1 ratio. Eudragit® is a polymer of methacrylic acid and methyl methacrylate available from Rohm Pharmo, Wetterstadt, Germany.

Figure 10:
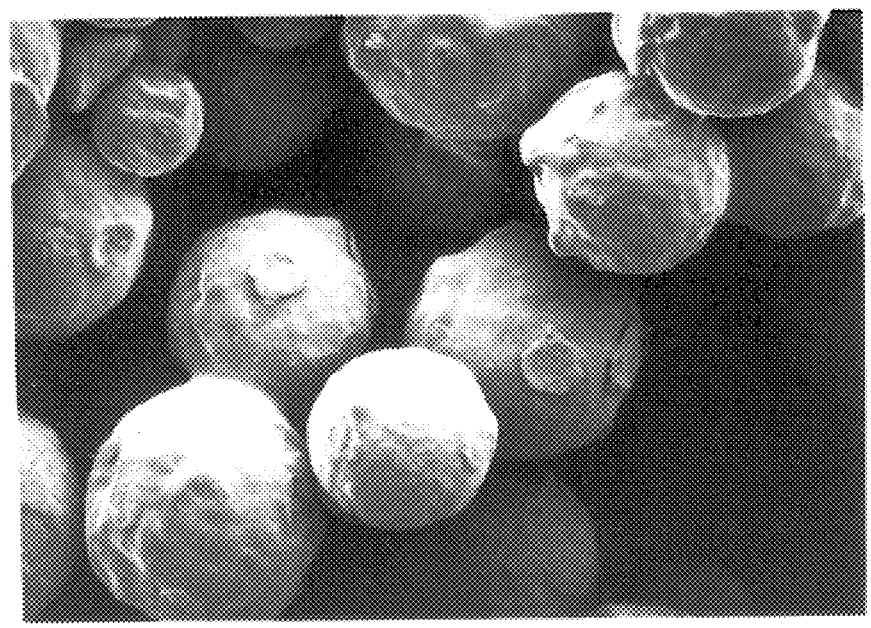
FIG. 10 is a photomicrograph at 125×magnification of another embodiment of the present invention in which microspheres produced in accordance with Example II have been coated.

The finished product provided 568 grams of finely coated acetaminophen beads. The coated product of the present example has been shown herein in FIG. 10 at 125× magnification. A very uniform coated product has been shown which can be easily used in feeding the coated active ingredient to machinery for tabletting and for the purpose of filling capsules.

Thin, uniform coatings such as that provided herein results in much less coating material required to obtain better resulting taste masking and controlled release. As a result of the monodispersed characteristic of the present product, there is less loss of product as a result of oversize material.

Coating in general is tremendously enhanced by providing a uniformly dispersed microsphere of the present invention. For example, in fluidized-bed type coating, the equilibrium condition established in the fluidized bed has a tendency to retain particles having a similar size for consistent and efficient coating. Thus, large and small particles outside the range of the uniform particle size leave the bed during coating. In that case, the active ingredient must be recycled and reprocessed to obtain the active ingredient for coating. In the present invention, non-uniform sizes are virtually eliminated.

Example IV

Ibuprofen Spheres

Using the same apparatus as shown in FIG. 5B, with a 60 mesh screen, ibuprofen was processed in accordance with the present invention.

An ibuprofen powder feedstock was fed to the spinning head and the head was rotated at about 4800 rpm while the heating elements were raised to a temperature which produced the liquiflash conditions. The feedstock also consisted of 15% Compritol 888 ATO and 5% Gelucire 50/13. (Compritol 888 ATO is a glycerol behenate NF made available by Gattefosse S.A., a French company. Gelucire is surfactant also available from Gattefosse S.A.).

Figure 11:
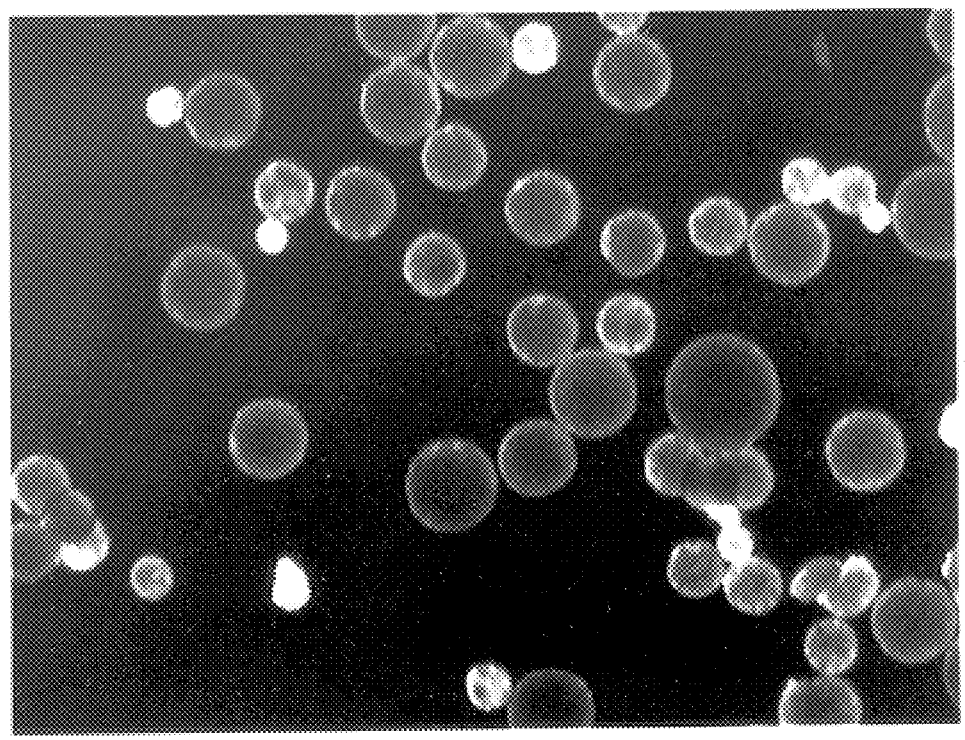
FIG. 11 is a photomicrograph at 50×magnification of ibuprofen shearlite product prepared in accordance with the present invention.

The spinning head forced the material through the screen and the product was permitted to free fall a distance of from 6–8 feet below the spinning head. The product collected is shown in the photomicrograph of FIG. 11 which has a magnification of 50×. As can be seen from FIG. 11, the spheres have a highly consistent particle size ranging from about 50–200 microns in diameter.

Figure 11A:
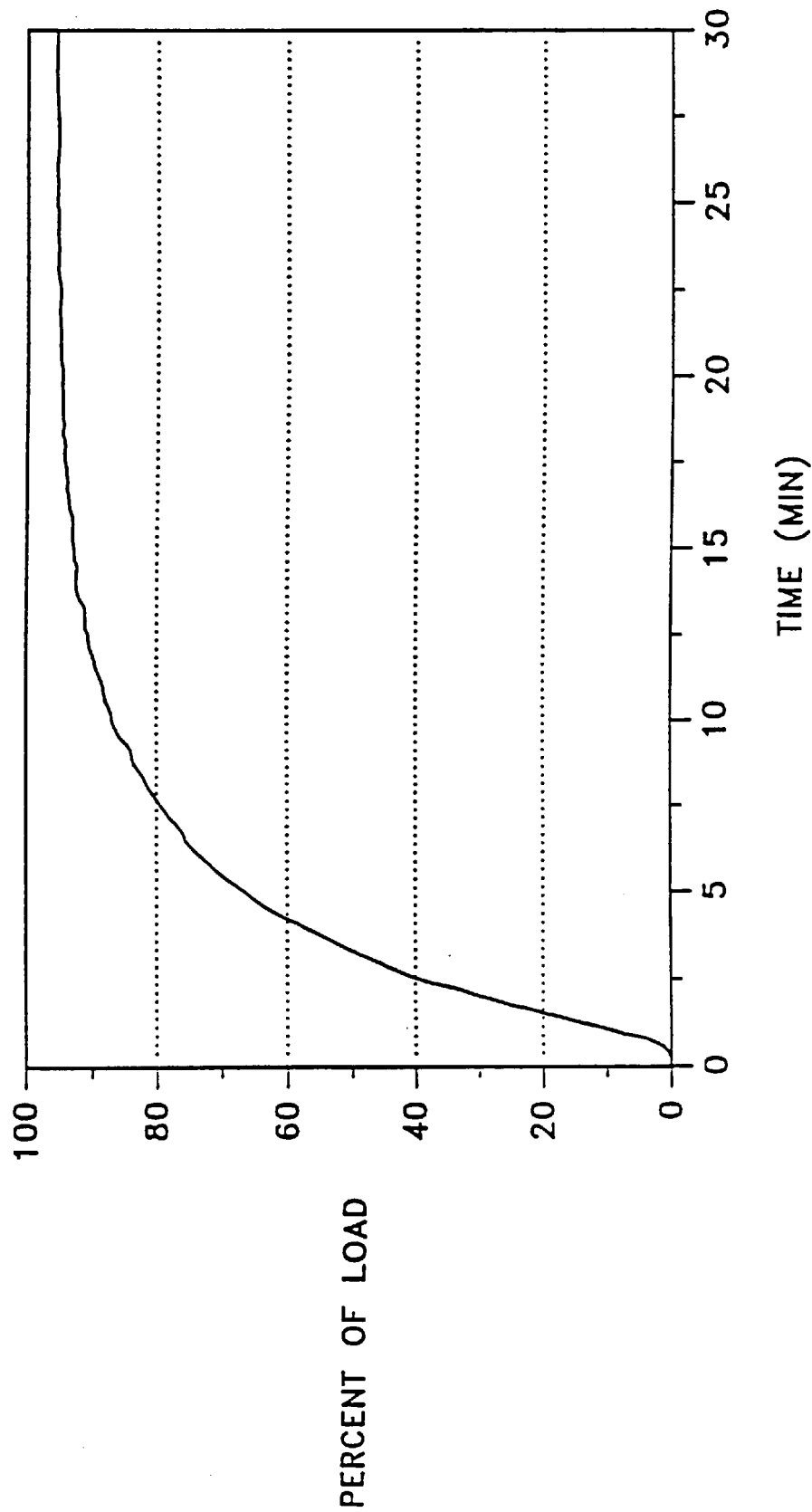
FIG. 11A is a graph which depicts dissolution of the ibuprofen shearlite product shown in FIG. 11.

The product was also subjected to dissolution testing to determine the time required for dissolution of the active ingredient. The monograph is provided by the U.S. Pharmacopoeial Convention, Inc. in the U.S. Pharmacopoeial National Formulary Monograph For Ibuprofen Dissolution Study, U.S. 23 NF 18, page 786 (1995). The results have been shown in FIG. 11A. At a composition level of 80% ibuprofen, it can be seen that the time for dissolution of most of the ibuprofen occurred at about 15 minutes and virtually total dissolution occurred at around 20–25 minutes. These results show high predictability for delivery to a bio-system by use of microspheres produced in accordance with the present invention.

Example V

Ascorbic Acid Spheres

In this Example, ascorbic acid was processed by the liquiflash process using the apparatus described in FIG. 5C. As a result of the short brass veins having a thickness of about 0.006 inches surrounding each of the heating elements, gaps of 0.002 inches were provided. Moreover, the head was positioned 10 feet from the collecting surface to permit an unobstructed formation and solidification of shearlite particles in accordance with the present invention.

Ascorbic acid powder was fed into the spinner revolving at about 1800 rpm while the head was heated to a point at which the powder was changed to liquiform for purposes of liquiflash processing. Fine beads were expelled from the spinning head. Bead formation began after about 15 seconds and the product formation was completed in about 15–20 seconds actual spinning time.

The bead size production was as follows: 0.10% retained on No. 10 mesh; 0.62% on No. 20 mesh; 21.10% on No. 40 mesh; 40.35% on No. 60 mesh; 23.10% on No. 80 mesh; and 14.70% passed through No. 80 mesh. Thus, it can be seen that a high degree of predictability of shearlites were produced from ascorbic acid using the process of the present invention.

Example VI

Ascorbic Acid Tablet Production Without A Binder

The ascorbic acids shearlite particles produced in accordance with Example V were classified according sieve size. The portion passing through the No. 80 mesh was used to feed a tabletting press. The tabletting press used was a Specac Model 15.011 tablet press.

Quite interestingly, the ascorbic acid product was able to be fed efficiently into the tablet press using a very small angle of repose. By angle of repose, it is meant the angle required to induce flow of the tablet feedstock into the tablet press. A low angle of repose is highly desirable for purpose of efficient processing.

Tablets were produced under 42 tons per square inch of pressure. The resulting tablets displayed excellent cohesiveness and have a shiny surface which exhibited no sticking during removal from the die. Moreover, the superior tablet product prepared as a result of the present invention did not require a binder or any other additive to ensure cohesiveness of the tablet.

Example VII

Pseudoephedrine Beads

Two experiments were run to determine the processability of pseudoephedrine as a feedstock material. The apparatus used in these examples is that depicted and described in FIGS. 4A, 4B, and 4C.

A feedstock consisting of 95% pseudoephedrine (Kroll 331151) and 5% polyethylene glycol (PEG 1450) was prepared by melting the polyethylene glycol and adding thereto the pseudoephedrine and blending and then permitting the mixtures to solidify. The solidified mixture was then powdered in a grinding apparatus.

The spinning head was spun at 3300 rpm and the feedstock material was introduced until the material was reduced to liquiflash condition. The product resulting therefrom was very uniform in shape and the majority of the spheres were around 160 microns.

Figure 12A:
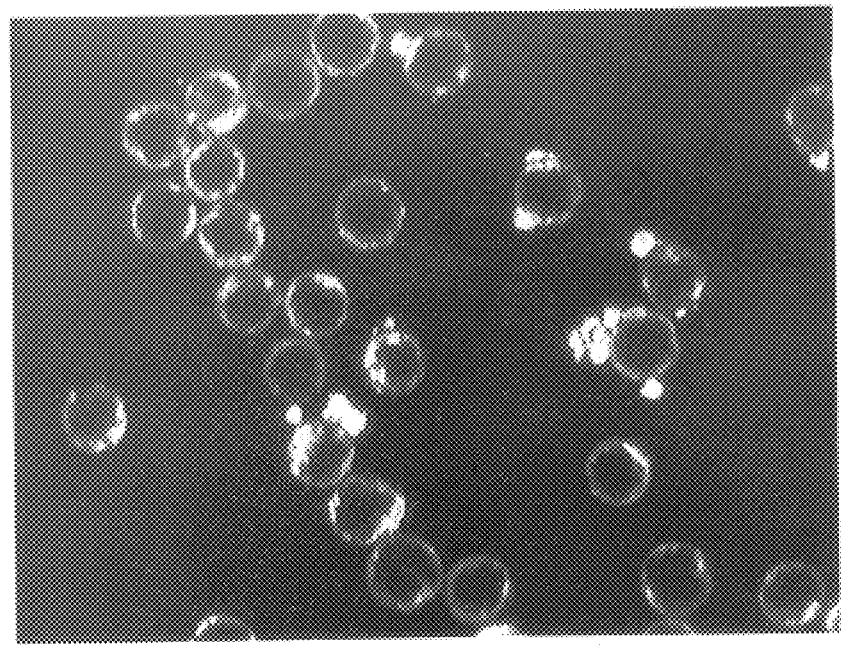
FIGS. 12A and 12B are photomicrographs at 50×magnification of pseudoephedrine prepared in accordance with the present invention.

The results of this first experiment are shown in the photomicrograph of FIG. 12A, and the dissolution characteristics have been depicted in 12C. As can be seen from these figures, the product was a very uniform spherical bead which demonstrated immediate dissolution of the active ingredient. The actual content of pseudoephedrine in the product shown in FIG. 12A and 12B was 95%.

A second portion of this example was performed using the same ingredients as reported in the first experiment and the outcome was also similar.

Figure 12B:
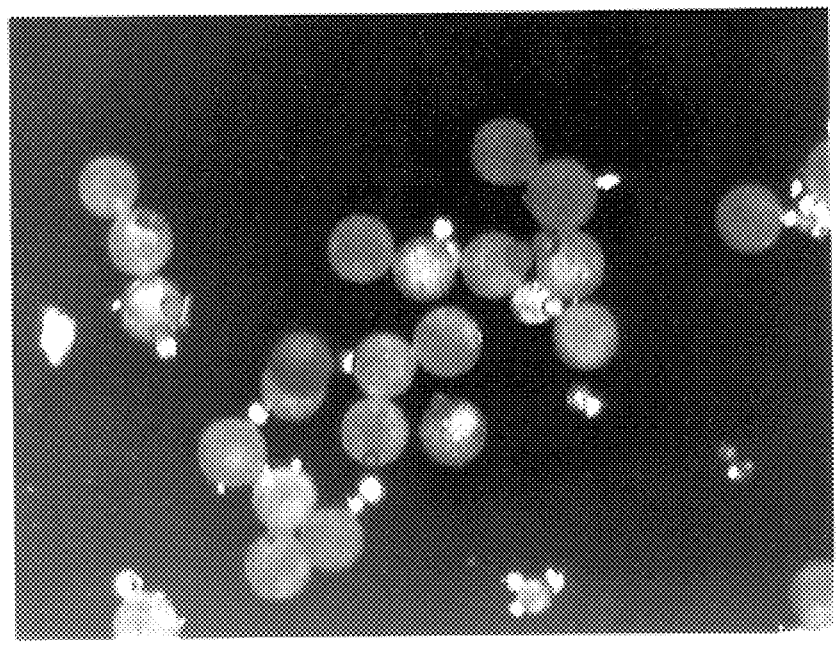
Figure 12C:
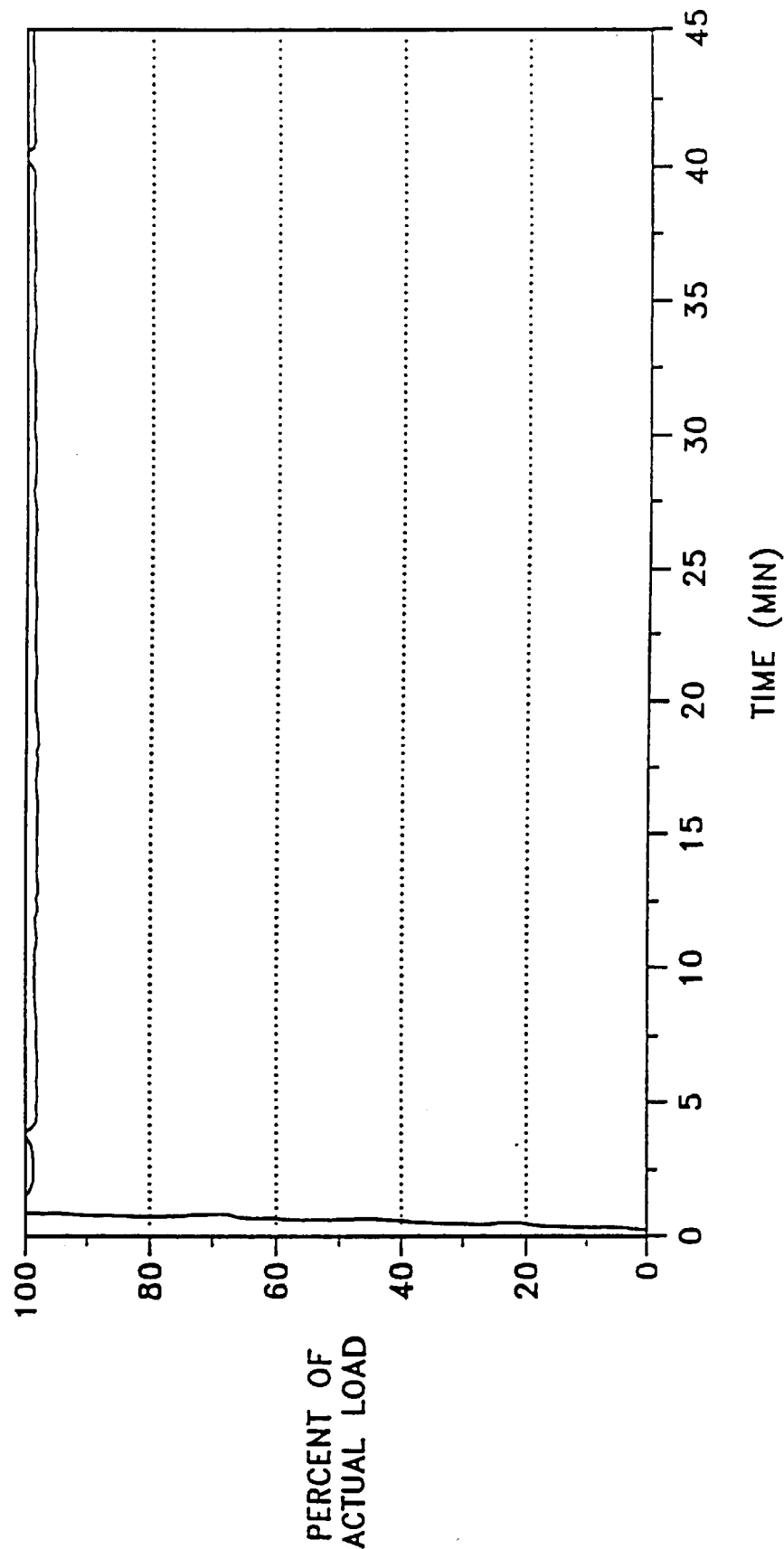
FIG. 12C is a graph which depicts the dissolution of the product shown in FIG. 12A.
Figure 12D:
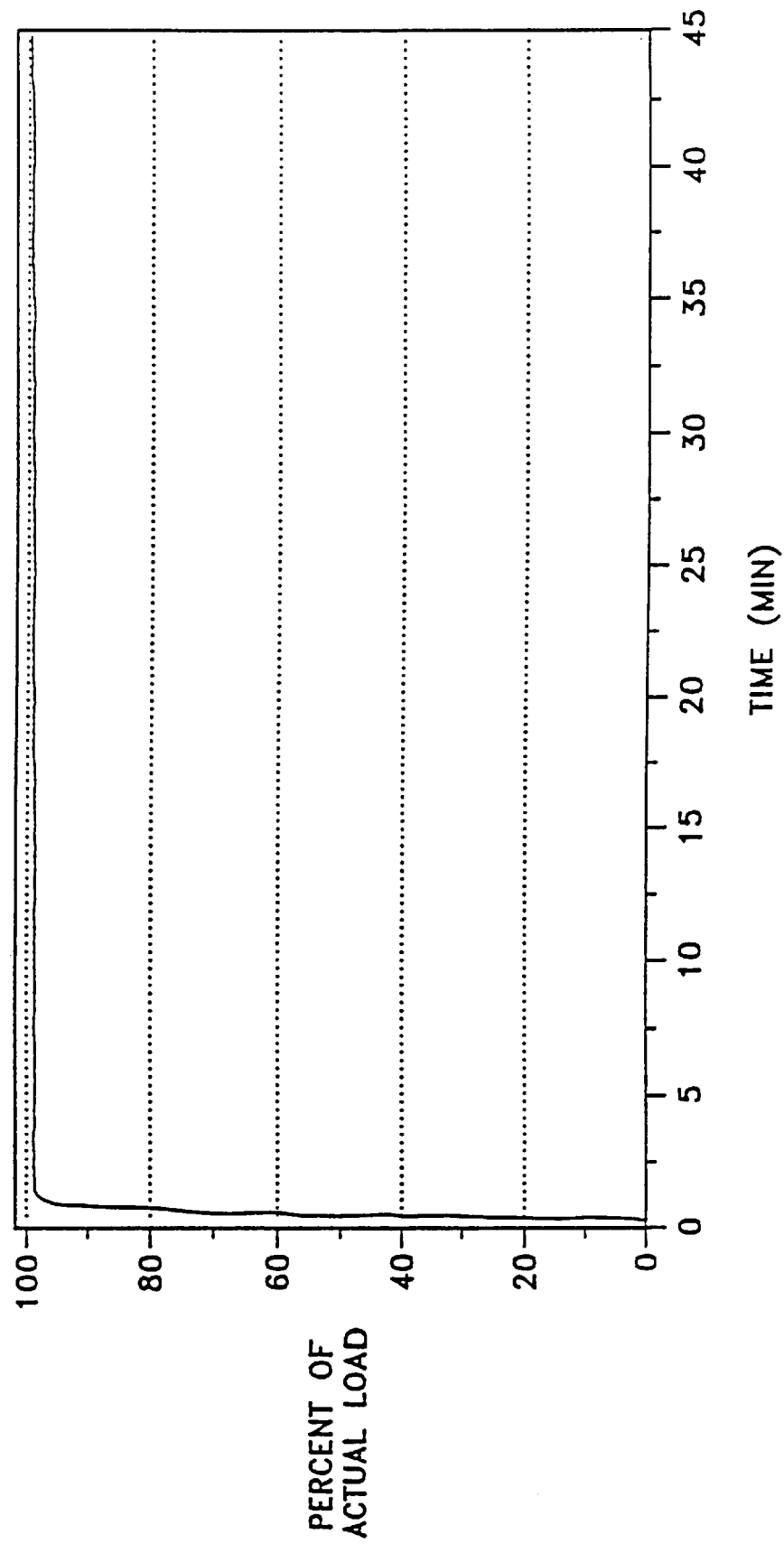
FIG. 12D is a graph which depicts the dissolution of the product shown in FIG. 12B.

The product, which has been shown here in FIG. 12B has a very uniform spherical shape having a size of between 160 and 180 μm. The actual content of active ingredient was 96.06%. The dissolution characteristics are shown in FIG. 12D which depicts an excellent and predictable release rate of the active ingredient.

Example VIII

Pseudoephedrine And Glycerol Monostearate

In this example, 30% pseudoephedrine and 70% glycerol monostearate (Myverol 18-06) was blended and introduced to the apparatus shown in FIG. 4A, 4B, and 4C. The head was spun at 3300 rpm and the temperature raised until the feedstock became liquiform.

Figure 13:
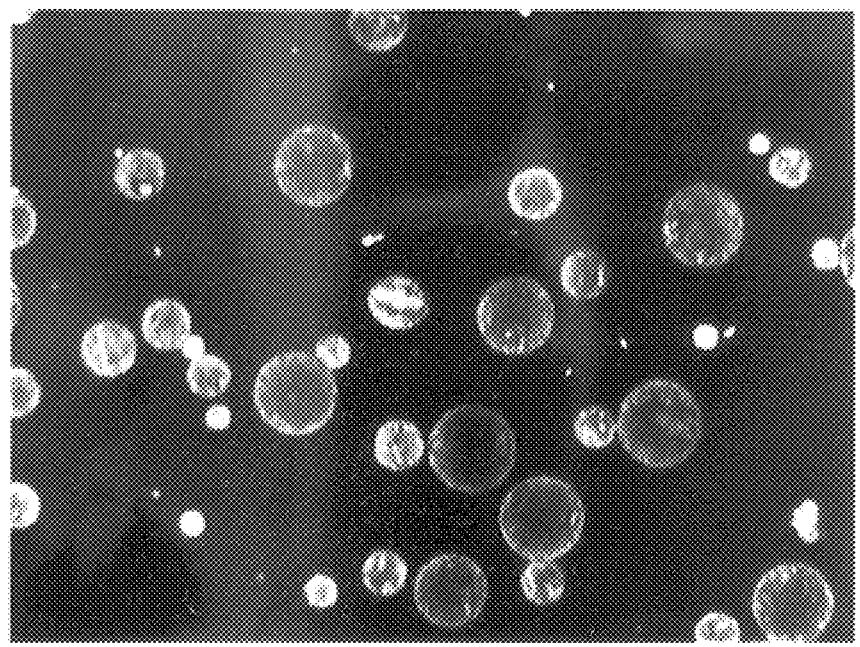
FIG. 13 is a photomicrograph at 50×magnification which depicts a pseudoephedrine product prepared in accordance with the invention.

The product formed as a result of the liquiflash processing was a uniform spherical product ideally suited for inclusion in a delivery system. The product is shown in FIG. 13, which is a photomicrograph taken at 50×magnification.

Example IX

Dextromethorphan and Glycerol Monostearate

In this example, the active, dextromethorphan, was mixed with glycerol monostearate (Myverol 18-06). Dextromethorphan HBr (30%) was mixed with 70% Myverol 18-06 brand glycerol monostearate blended and then introduced to a spinning head as described above.

Figure 14:
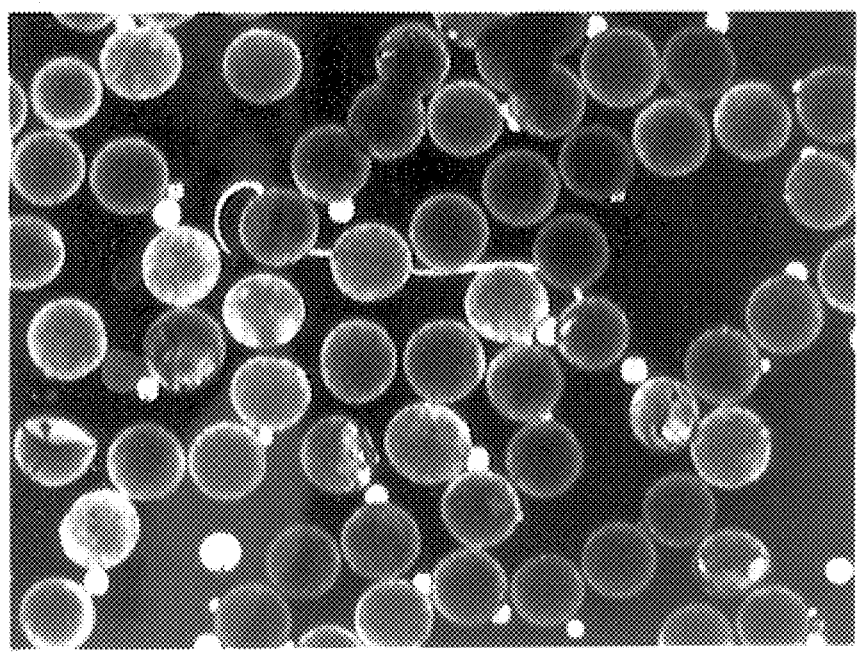
FIG. 14 is a photomicrograph at 50×magnification of a dextromethorphan product prepared in accordance with the present invention.

The spinning head was run at 3300 rpm and the temperature raised until the feedstock was processed as a liquiform. Spheres appeared as two major size groups, one at the 40 to 80 micron range and another group at the 160–200 micron range. These two groups were very uniform in shape and many spheres showed small crystalline particles encapsulated within them. The product was very clean and have been shown in the photomicrograph at 50×magnification in FIG. 14.

Example X

Dextromethorphan-Pseudoephedrine Amalgam

In this example, a cough and cold treatment was produced by preparing an amalgam from pseudoephedrine and dextromethorphan. Shearlite particles were made from the two active ingredients. Dextromethorphan HBr and pseudoephedrine HCl were mixed with Myverol 18-06 in amounts which provided 12.5% dextromethorphan, 25% pseudoephedrine, and 62.5% Myverol. The active agents were mixed and then added to Myverol after which they were blended. The blend was then subjected to liquiflash processing at 3300 rpm in an apparatus shown in FIGS. 4A–C.

Figure 15:
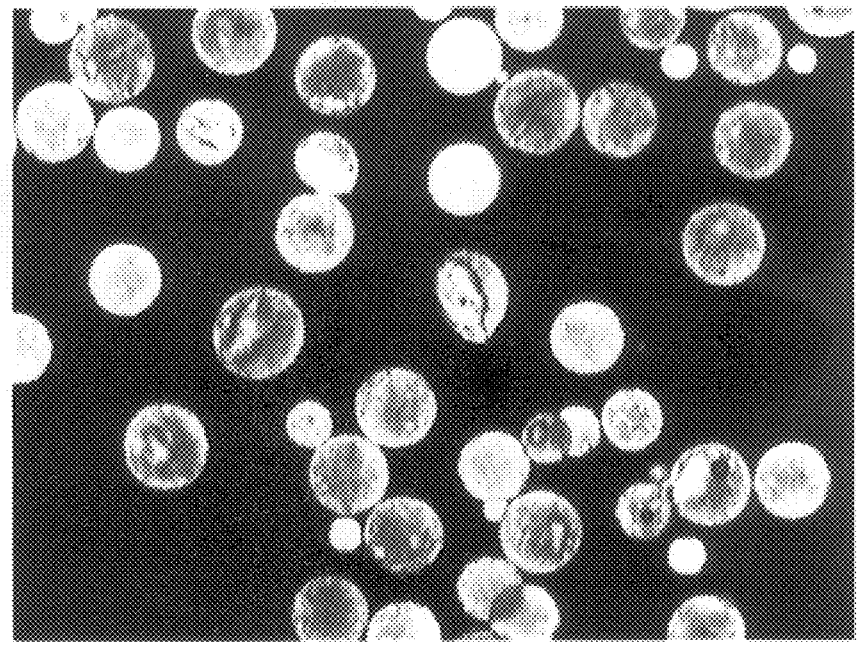
FIG. 15 is a photomicrograph taken at 50×magnification of amalgam of shearlite particles containing a cough and cold treatment formed in accordance with the present invention.

The product was a shearlite particle very uniform in shape and size. Two size groups were produced, one between 20 and 80 microns and another between 120 and 220 microns. A photomicrograph of the product is shown in FIG. 15.

The product was an excellent amalgam which can be used as a cough and cold medicinal treatment.

Example XI

Chloropheniramine-Diphenhydramine-Pseudoephredine Amalgam

In this example, the active ingredients were combined to provide another cough and cold treatment medicament. In particular, chloropheniramine maleate was combined at a rate of 2.8% with 17.5% diphenhydramine HCl and 21% pseudoephredine HCl in combination with 58.7% Myverol 18-06. The active ingredients were blended and then mixed with Myverol and again blended.

Figure 16:
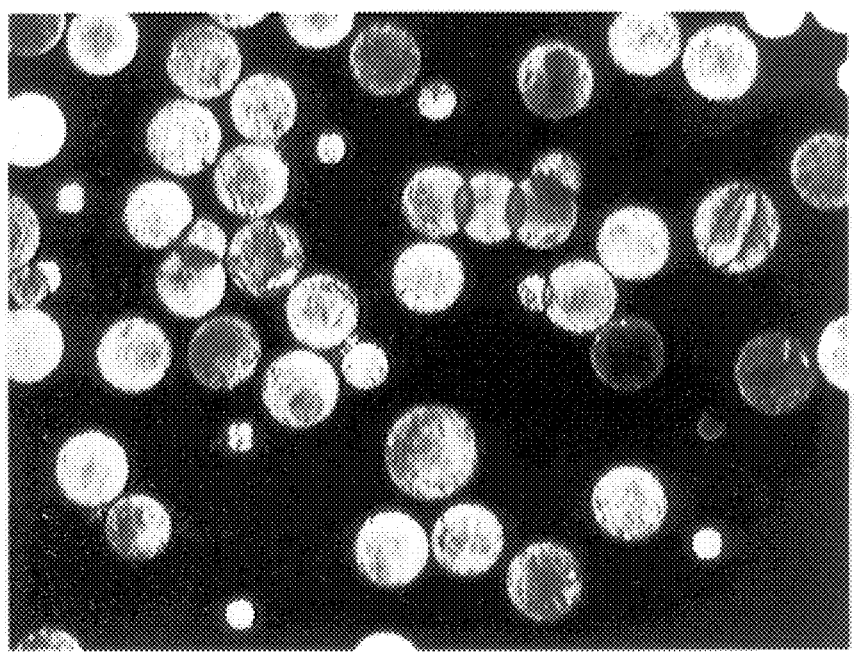
FIG. 16 is a photomicrograph taken at 50×magnification of spheres formed from an amalgam of three (3) active ingredients (also a cough and cold treatment) in accordance with the present invention.

The resulting mixture was liquiflash processed in an apparatus such as that shown in FIGS. 4A–C at 3300 rpm. Photomicrographs of the products produced in accordance with this example are shown in FIG. 16.

Excellent shearlite particles were produced with the combination of the three drugs. Two major size ranges were produced, one at 40–80 microns and another at 160–220 microns.

This example shows that true amalgams can be formed of different active ingredients to provide medicinal treatments to suit the medical practitioner. Furthermore, coatings can be provided as desired in accordance with the present invention. Thus, controlled-release and taste masking can be effected by coating the shearlite particles.

Example XII

Taste Comparison of Coated Unprocessed Ibuprofen and Coated Processed Ibuprofen

Raw ibuprofen feedstock was coated with Ethocel™ brand ethylcellulose:PVP blend at 90:10 ratio. The coating were deposited at a rate of 10% coating. Furthermore, ibuprofen shearlite particles prepared as set forth in Example IV were also coated at a rate of 10% coating with Ethocel™ brand coating.

Products resulting from both coating procedures were then subjected to a taste panel to determine whether or not effective taste masking had been accomplished. In a comparison between the two products, it was found that the raw ibuprofen was not effectively taste masked, while the processed ibuprofen had a high degree of taste masking.

Moreover, upon microscopic inspection, it was seen that the coating on unprocessed ibuprofen was uneven, whereas the processed ibuprofen was evenly coated with a thin coating of the Ethocel™ brand coating.

Therefore, it can be seen that active agents converted to shearlite particles by being subjected to liquiflash conditions provide a excellent substrate for applying coating which masks the unappealing taste of the active agent.

Example XIII

Demonstration of Enhanced Flowability

Experiments were also conducted to demonstrate the enhanced flowability resulting from subjecting a feedstock material to liquiflash processing.

In one method, a flow rate test was conducted by using a funnel having a set diameter of 20 millimeters at the outlet thereof. A measured weight of raw feedstock, i.e, 30 grams, was poured into the funnel while blocking the outlet side. The flow was then timed upon unblocking the outlet. The active ingredients used in the test were acetaminophin and ibuprofen.

Shearlite particles of both ingredients were prepared using the apparatus shown in FIGS. 4A–C. The ibuprofen was processed using 80% ibuprofen, 15% Compritol 888 ATO and 5% Gelucire. Acetaminophin was processed without the addition of other ingredients.

The unprocessed ibuprofen and acetaminophin did not flow from the exit opening of the funnel even after administering tapping on the side of the funnel.

Both the ibuprofen and the acetaminophine which had been processed under liquiflash conditions, however, exit the opening of the funnel. The ibuprofen formula required one tap on the top of the funnel and the entire 30 grams emptied in only one second. The processed acetaminophin required no tapping on the funnel and passed through the exit opening of the funnel in less than one second.

Thus, the present invention can be seen to be highly effective in improving the flow characteristic of active ingredients.

Example XIV

Further Demonstration of Improved Flow Characteristic

In this example raw active agent and shearlite particles were tested to compare improvement of the angle of repose. Thus, the ability of the raw material to flow was directly compared to the flowability of the shearlite particle resulting from the present invention.

The method used to measure the angle of repose is a fixed cone method. Reference: "Multi-Particle Oral Drug Delivery," Isaac Ghebre-Sellassie, Vol. 65, Marcel Dekker, Inc., New York. In this method, powder is dropped through a funnel at a controlled distance from a dish which has vertical sides. The powder is poured until it just touches the tip of the funnel. The radius of the powder circle in the dish and the height to the tip of the funnel are measured. The comparison test were run by clamping a funnel 14 millimeters above the bottom of the glass petri dish. The angle of repose is then calculated using the following equation Tan $\phi = h/r$ or $\phi = \text{Arctan } h/r$.

The results of the test indicated that only the shearlite particles of acetaminophine and ibuprofen flowed through the funnel and therefore possess a measurable angle of repose. The angle of repose is also very low, i.e., less than 45°.

The results of the flow test have been set forth hereinbelow in the angle of repose table.

| Material | Flow Rate | Angle of Repose |
|---|---|---|
| Processed APAP | less then 1 second | 19.53° |
| 100% Non-Processed APAP | No Flow | NA |
| Processed Ibuprofen | 1 second | 22.93° |

-continued

| Material | Flow Rate | Angle of Repose |
|---|---|---|
| Unprocessed Ibuprofen | No Flow | NA |
| 100% Ibuprofen Drug Unprocessed | No Flow | NA |

It can be seen that the process of the present invention provides an active ingredient with significantly enhanced flow characteristic. Basically, it converts non-flowable material to flowable material and improves flowability where there is little or no flow capability.

Example XV

Sucrose/Mannitol Spheres

Following the procedure of Example I, a 50—50 weight percent (wt. %) mixture of granulated sucrose and mannitol were subjected to liquiflash conditions utilizing a spinning head at 3600 rpm at approximately 195° C. The resulting product was 100% distribution of solid spheres. These solid spheres, as in Example I, ranged in size from about 100 to about 200 µm in diameter. These spheres are substantially solid throughout, and can be used in the variety of ways, such as an excipient in the production of dosage units. More importantly, the use of a 50—50 wt. % mixture of sucrose and mannitol facilitated 100% distribution of spheres. Thus, the utilization of a 50—50 wt. % mixture of sucrose and mannitol facilitated a more efficient production of the shearlite particles of the present invention.

Example XVI

Direct Tableting Example

Acetaminophen shearlite particles, i.e., microspheres, prepared in accordance with Example II were used to determine whether or not direct tableting of acetaminophen microspheres could be accomplished. The present example set forth the results of an attempt to deliver the acetaminophen microspheres directly to a tableting machine and compressing under pressures of from 0.5 to 5 tons of force. In order to prepare the microspheres for tableting, 500 grams of 100% acetaminophen microspheres were passed through a 40 mesh screen and combined with approximately 26.5 grams of sodium starch glycolate sold under the trademark EXPLOTAB® by Edward Mendell Co.

The microsphere material was fed directly to a single press twelve (12) millimeter die and punch tableting apparatus. Compaction forces of from 0.5 tons to 5 tons were used, i.e., 0.5 ton, 1 ton, 2 tons, 3 tons, 4 tons and 5 tons of pressure.

The tablets made in accordance with the present example displayed no capping or cracking and were rated as "non-sticky" to the tableting apparatus. Moreover, the tablet mixture was free flowing and easily directed to the twelve (12) millimeter die.

Each of the tablets were then immersed in an aqueous environment and permitted to dissolve. As expected, tablets compressed at 0.5 tons dissolved somewhat faster, while the tablets prepared under increasingly greater compaction pressure disintegrated more slowly.

It is also important to note that in the present example, the microspheres used for tableting readily flowed into the die cavity and are considered suitable for feeding into automated tabletting machines. Thus, the experiment reported herein in Example XV demonstrates the ability to subject microspheres to direct tabletting without requirement of additional interim steps usually required to effect tabletting in tabletting machines.

SHEARLITE EXCIPIENT EXAMPLES

In accordance with the present invention various active-containing tabletting formulations were prepared using excipient shearlite particles and active-containing shearlite particles. A summary of the range of ingredients to be used is shown in Table 1.

TABLE 1

| Ingredients | Range | Preferred Range |
|---|---|---|
| Excipient Shearlite Particles | 0–99 wt. % | 49.25–85 wt. % |
| Active-Containing Shearlite Particles | 1–100 wt. % | 15–50 wt. % |
| Flavoring Agents (Including Sweeteners) | 0–20 wt. % | 0.5–15 wt. % |
| Other Ingredients (E.g., Humectants, Flow Agents, Binding Agents, Etc) | 0–15 wt. % | 0.25–6 wt. % |

Example XVII

Ibuprofen Tablets Utilizing Amorphous Sucrose Spheres

Ibuprofen tablets were prepared utilizing the amorphous sucrose spheres (shearlite particles) prepared in accordance with Example I, and Ibuprofen shearlite particles. The Ibuprofen shearlite particles were formed from a composition containing 88 wt. % ibuprofen, 10 wt. % Compritol 888, 2 wt. % Gelucire 50/13 core with a 12 wt. % coating of Eudragit® NE 30D, HPMCP, microtalc, and adipic acid, to produce a composition having 77.4 wt. % total active ingredient.

The tabletting formulation was prepared in the following manner. First, approximately 34.44 wt. % of ibuprofen shearlite particles was measured, to which 2.0 wt. % glycerin (a binding agent) was added thereto. This mixture was agitated by hand for approximately 30 seconds. The mixture was then placed in a turbulent mixer and agitated for approximately three minutes. Thereafter, 61.56 wt. % sucrose shearlite particles was measured and added to the ibuprofen particles in ⅓ increments. The mixture was agitated in the turbulent mixer after each addition. After the addition of the last increment, 0.5 wt. % lemon flavoring agent, 0.5 wt. % whipped cream flavoring agent, 0.5 wt. % aspartame and 0.5 wt. % citric acid were added to form a 100 wt. % mixture. The resulting mixture was then reagitated for approximately two minutes in the mixer.

The tabletting formulation was then fed directly into a single press 18 millimeter die and punch tabletting apparatus. Tablets were formed utilizing 60 pounds per square inch (psi) at a 0.2 second compression duration. The resulting product of the compression were tablets that were too thin. This procedure was then repeated utilizing a 15 millimeter die and punch tabletting apparatus. The resulting tablets exhibited satisfactory cohesion.

To ascertain if tablet hardness could be improved by an increase in compression force, the above procedure was repeated utilizing increased compression forces. A first run was conducted utilizing a compression force of 80 psi with a 15 millimeter die and punch tabletting apparatus for a compression duration of 0.2 seconds. The resulting tablets exhibited an improved hardness in comparison to the tablets produced with a compression force of 60 psi. The compression duration was subsequently increased to 0.6 seconds to ascertain if an improvement in hardness could be achieved. The increased duration of compression did not effect the tablet hardness. The compression force was increased to 100 psi with a compression duration of 0.2 seconds. As a result of this increased compression force, a greater effort was required to remove the tablets from the tabletting apparatus. Thus, a compression force of 80 psi at a compression duration of 0.2 seconds provided the best results in tablet formation.

Example XVIII

In an attempt to improve extraction of the tablets from the tabletting apparatus, various concentrations of a flow agent, magnesium stearate, were added to the tabletting formulation of Example XVII. In a first run, 0.5 wt. % of magnesium stearate was added to a sample of the tabletting formulation of Example VIII. The tabletting formulation was fed to a 15 millimeter die and punch apparatus operating at 100 psi. A compression duration of 0.2 seconds was utilized to form the tablets. This procedure was then repeated utilizing a sample of tabletting formulation from Examples XVII with 1.0 wt. % of magnesium stearate. An improvement tablet extraction from the tabletting apparatus was exhibited with both formulations.

Example XIX

An ibuprofen tabletting formulation in accordance with the tabletting formulation of Example XVII was prepared with a decreased concentration of glycerin (i.e., binding agent). The tabletting formulation contained 62.56 wt. % amorphous sucrose spheres, 34.44 wt. % ibuprofen, 1.0 wt. % glycerin, 0.5 wt. % lemon flavoring agent, 0.5 wt. % whipped cream flavoring agent, 0.5 wt. % Aspartame and 0.5 wt. % citric acid, to give a 100 wt. % formulation. The formulation was free flowing and was easily directed to the 15 millimeter die and punch. A compression force of 100 psi for a compression duration 0.2 seconds was utilized. As in Example XVII, the greater compression force required an increased effort to extract the tablets from the tabletting apparatus. Otherwise, the resulting tablets were satisfactory.

Example XX

An ibuprofen tabletting formulation in accordance with of Example XIX was prepared having a further decreased glycerin concentration. The formulation contained 63.06 wt. % amorphous sucrose spheres, 34.44 wt. % ibuprofen, 0.5 wt. % glycerin, 0.5 wt. % lemon flavoring agent, 0.5 wt. % whipped cream flavoring agent, 0.5 wt. % aspartame, and 0.5 wt. % citric acid. Tablets were formed utilizing the procedure described in Example XIX. As in Example XIX, the resulting tablets required an increased effort to extract the tablets from the tabletting apparatus. Otherwise, the resulting tablets were satisfactory.

Example XXI

In an attempt to improve extraction of the tablets from the tabletting apparatus 0.5 wt. % magnesium stearate as a flow agent was added to a sample of the ibuprofen composition of Example XIX. The formulation exhibited excellent flow properties and was easily directed to the 15 millimeter die. A compression force of 100 psi was utilized for a compression duration of 0.2 seconds. The formed tablets exhibited satisfactory cohesion and were easily extracted from the tableting apparatus.

Example XXII

An ibuprofen tableting formulation was prepared with a sample of the composition of Example XIX with 1.0 wt. % magnesium stearate as a flow agent. The formulation was tableted singularly on a half inch FFBE punch. Although the tablets exhibited a high friability, they were easily extracted from the tableting apparatus.

Example XXIII

An ibuprofen tableting formulation was prepared utilizing a heat spun floss as a supplement to the sucrose shearlite particle excipient of the present invention in order to ascertain the effects on tablet production. The formulation contained 30.8 wt. % floss having 3 wt. % lactose and 12 wt. % sorbitol therein, 30.8 wt. % the amorphous sucrose spheres, 34.4 wt. % ibuprofen, 2.0 wt. % glycerin, 0.5 wt. % lemon flavoring agent, 0.5 wt. % whipped cream flavoring agent, 0.5 wt. % aspartame and 0.5 wt. % citric acid. The formulation was tableted utilizing a 15 millimeter die and punch at a compression force of 100 psi for a compression duration of 0.2 seconds. The tableting formulation exhibited poor flow qualities and clumped together. The formed tablets also exhibited a patchy character, which was unsatisfactory.

Example XXIV

An ibuprofen tableting formulation was prepared having 50.0 wt. % amorphous sucrose spheres, 34.4 wt. % ibuprofen, 12.6 wt. % xylitab, 1.0 wt. % glycerin, 0.5 wt. % lemon flavoring agent, 0.5 wt. % whipped cream flavoring agent, 0.5 wt. % aspartame and 0.5 wt. % citric acid. The formulation was tableted utilizing a 15 millimeter die and punch at a compression force of 100 psi for a compression duration of 0.2 seconds. However, in this example, compression was repeated twice, i.e., two hits per tablet, instead of once as in the previous examples. The resulting tablets exhibited a high friability and crumbled, and were, therefore, unsatisfactory.

Example XXV

An ibuprofen tableting formulation having pure sucrose floss as a supplement to the sucrose shearlite particle excipient was prepared. The composition contained 50.0 wt. % amorphous sucrose spheres, 34.4 wt. % ibuprofen, 12.6 wt. % sucrose floss, 1.0 wt. % glycerin, 0.5 wt. % lemon flavoring agent, 0.5 wt. % whipped cream flavoring agent, 0.5 wt. % aspartame and 0.5 wt. % citric acid. The composition was tableted using a 15 millimeter die and punch at a compression force of 100 psi for a compression duration of 0.2 seconds. As in Example XXIV, two compressions were utilized in tablet formation. The resulting tablets exhibited a grainy and porous surface appearance, which was unsatisfactory.

Example XXVI

An ibuprofen tableting formulation as described in Example XXV was produced with the addition of 0.5 wt. % magnesium stearate as a flow agent. The composition was tableted using a 15 millimeter die and punch with a compression force of 100 psi for a compression duration of 0.2 seconds. Compression was repeated twice as in Examples XXIV and XXV. The resulting tablets exhibited a grainy surface and crumbled. Thus, the tablets were considered unsatisfactory.

Thus, while there have been described what are presently believed to be the preferred embodiments of the present invention, those skilled in the art will appreciate that other and further modifications can be made without departing from the true spirit of the invention, and it is intended to include all other such modifications and changes as come within the scope of the invention as set forth in the appended claims.

What is claimed:

1. A process for making a dosage unit, which comprises: directly tableting shearlite particles without intermediate processing or additional ingredients sufficiently to form a dosage unit, wherein said shearlite particles are provided by the process including the steps of:

a) subjecting a solid, organic-based feedstock, capable of being transformed to a liquiform in the substantial absence of dissolving medium, to liquiflash conditions which transforms said feedstock from a solid to a liquid to a solid under conditions of heat and centrifugal force to provide substantially unimpeded internal flow of said feedstock while liquefied and said liquefied feedstock having a viscosity such that all impedance to form liquid droplets is eliminated; said transformation occurring in not greater than five (5) seconds; and b) imparting shear force on said flowing feedstock in step "a" in an amount sufficient to separate particles by natural mass separation of said flowing feedstock in the presence of said shear force impinging thereon while in said unimpeded-flow condition.

2. The process of claim 1 wherein said discrete particles are microspheres.

3. The process of claim 1 wherein said liquiflash conditions are provided by spinning said feedstock in a spinning head having a heated peripheral barrier with exit openings for passage of flowing feedstock therethrough in the presence of centrifugal force provided by spinning said head.

4. The process of claim 1 wherein said shear force is imparted to said flowing feedstock by the resistance of ambient atmosphere against said flowing feedstock as it exits said spinning head.

5. The process of claim 1 which further comprises cooling said separated particles.

6. The process of claim 1 wherein said discrete particles are monodispersed such that at least about 40% by weight of the particles have a largest particle diameter within 60% of the mean particle diameter.

7. The process of claim 1 wherein said feedstock comprises a medicament, an excipient and mixtures thereof.

8. The process of claim 7 wherein said medicament is selected from the group of active agents consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, antiemetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, $H_2$-antagonists, anti-uricemia drugs and mixtures thereof.

9. The process of claim 1 wherein said directly tableting comprises transport of shearlite particles from a shearlite forming process to a tableting process.

10. The process of claim 1 wherein said shearlite particles comprise shearlite particles of a medicament and shearlite particles of an excipient.

11. The process of claim 10 wherein said excipient shearlite particles are formed from a feedstock of a saccharide based material.

12. A process for making a dosage unit which comprises:
tableting shearlite particles sufficiently to form a dosage unit, wherein said shearlite particles are provided by a process which includes the steps of:

a) subjecting a solid, organic-based feedstock, capable of being transformed to a liquiform in the substantial absence of dissolving medium to liquiflash conditions which transforms said feedstock from a solid to a liquid to a solid under conditions of heat and centrifugal force to provide substantially unimpeded internal flow of said feedstock while liquefied and said liquefied feedstock having a viscosity such that all impedance to form liquid droplets is eliminated; said transformation occurring in not greater than five (5) seconds;

b) imparting shear force on said flowing feedstock in step "a" in an amount sufficient to separate particles by natural mass separation of said flowing feedstock in the presence of said shear force impinging thereon while in said unimpeded flow condition; and c) coating or adding at least one excipient to the particles resulting from step "b".

* * * * *